US005639630A

United States Patent [19]
Malin et al.

[11] Patent Number: 5,639,630
[45] Date of Patent: Jun. 17, 1997

[54] METHOD AND REAGENT COMPOSITION FOR PERFORMING LEUKOCYTE DIFFERENTIAL COUNTS ON FRESH AND AGED WHOLE BLOOD SAMPLES, BASED ON INTRINSIC PEROXIDASE ACTIVITY OF LEUKOCYTES

[75] Inventors: Michael J. Malin, Park Ridge, N.J.; Phyllis Shapiro, Yorktown Heights, N.Y.; John F. Cremins, Waterbury, Conn.

[73] Assignee: Bayer Corporation, Tarrytown, N.Y.

[21] Appl. No.: 442,491

[22] Filed: May 16, 1995

[51] Int. Cl.$^6$ ............... C12Q 1/28; C12Q 1/34; C12N 5/00; G01N 33/48
[52] U.S. Cl. ............... 435/28; 435/18; 435/15; 435/4; 435/7.24; 435/40.51; 436/63; 436/74; 436/17; 436/16
[58] Field of Search ............... 435/28, 18, 15, 435/4, 7.24, 240.1, 240.2; 436/63, 74, 17, 16

[56] References Cited

U.S. PATENT DOCUMENTS

| | | | |
|---|---|---|---|
| 3,741,875 | 6/1973 | Ansley et al. | 435/28 |
| 4,099,917 | 7/1978 | Kim | 435/28 |
| 4,801,549 | 1/1989 | Cremins et al. | 436/63 |
| 4,978,624 | 12/1990 | Cremins et al. | 436/63 |
| 5,116,539 | 5/1992 | Hamaguchi et al. | 436/63 |
| 5,116,734 | 5/1992 | Higgs et al. | 435/28 |
| 5,128,265 | 7/1992 | Meiattini | 436/17 |
| 5,232,857 | 8/1993 | Lefevre et al. | 436/17 |
| 5,262,302 | 11/1993 | Russell | 435/28 |
| 5,264,369 | 11/1993 | Saka et al. | 436/63 |
| 5,389,549 | 2/1995 | Hamaguchi et al. | 436/63 |
| 5,426,029 | 6/1995 | Rittershaus | 435/7.24 |
| 5,518,928 | 5/1996 | Cremins et al. | 436/63 |
| 5,525,461 | 6/1996 | Rittershaus | 435/7.24 |
| 5,538,893 | 7/1996 | Sakata et al. | 436/17 |

OTHER PUBLICATIONS

Technicon® Technical Publication No. UAB-3515-00, Product Labeling Technicon H6000 System (90/h), Section I, pp. 1-8, Apr., 1993.
Technicon® Addendum No. TK81-443-20, Technical Publication No. UA81-443B00, Addendum to vol. II of the Product Labeling for the Technicon H6000 System.

*Primary Examiner*—John Kight
*Assistant Examiner*—Louise Leary
*Attorney, Agent, or Firm*—Morgan & Finnegan, L.L.P.

[57] ABSTRACT

The present invention provides an improved reagent composition and method to perform white blood cell differential counting and subpopulation analysis using both fresh and aged blood samples with accuracy and precision. The invention is particularly applicable for the analysis of aged blood samples that have been stored at room temperature for over a day, thereby allowing accurate and useful information to be obtained from samples that are normally considered to be suboptimal. The improved reagent composition and method are particularly related to the peroxidase method of white blood cell differential determinations. One aspect of the invention includes an improved aqueous reagent composition for carrying out the peroxidase method of differential counting. Another aspect includes the use of a rinse cycle and rinse solution devoid of hemolytic surfactant to alleviate the adverse effects of rinse carryover and to streamline and economize the analytical process, particularly when the analyses are performed on automated hematology analyzers and flow cytometry systems. The composition and method of the invention provide clinically useful data for the differential analysis of whole blood samples.

80 Claims, 4 Drawing Sheets

FIG. IA
DAY 1 SAMPLE
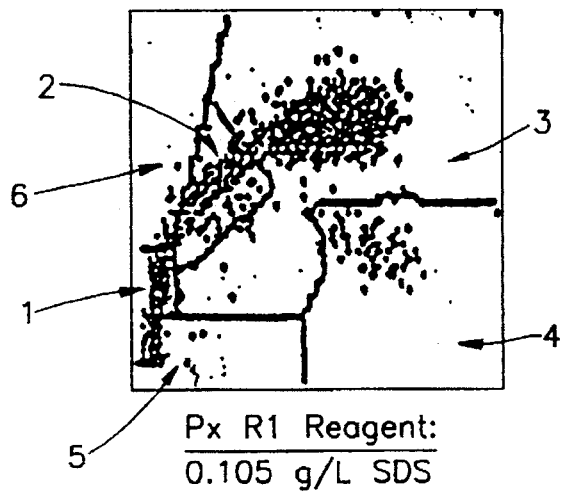
Px R1 Reagent:
0.105 g/L SDS
Rinse: 3.0 g/L Brij 35 and 2.0 g/L SDS
FIG. IB
DAY 2 SAMPLE
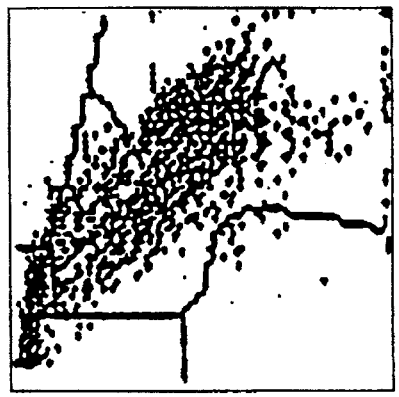
Px R1 Reagent:
0.105 g/L SDS
Rinse: 3.0 g/L Brij 35 and 2.0 g/L SDS
FIG. IC
DAY 2 SAMPLE
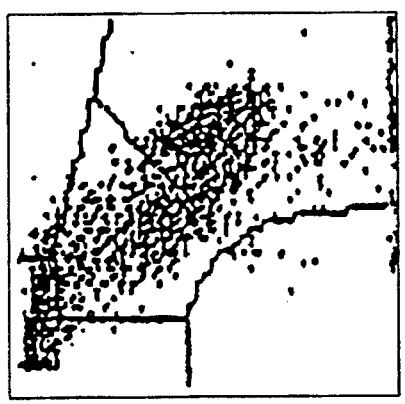
Px R1 Reagent:
0.105 g/L SDS
Rinse: 1.0 g/L Pluronic P105 in PBS
FIG. ID
DAY 2 SAMPLE
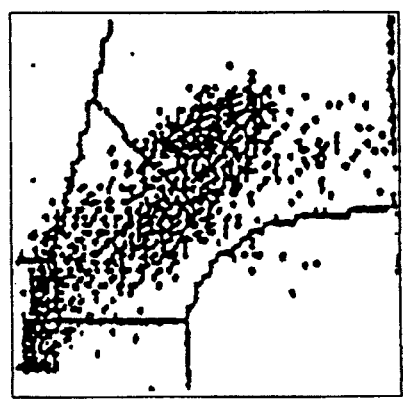
Px R1 Reagent:
0.17 g/L SDS
Rinse: 1.0 g/L Pluronic P105 in PBS

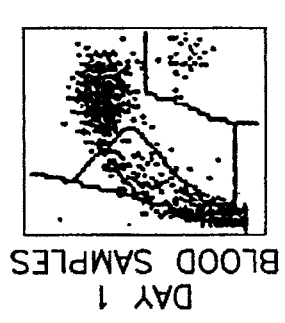
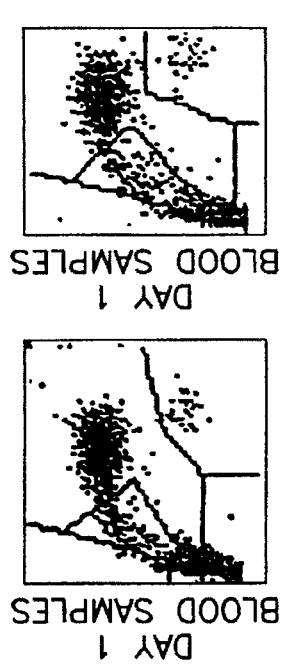
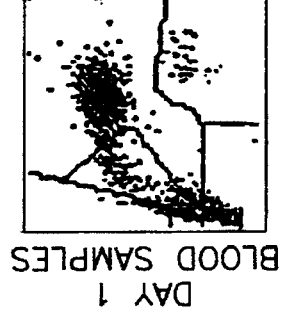
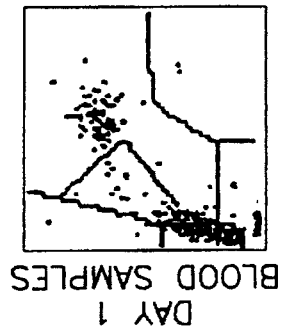
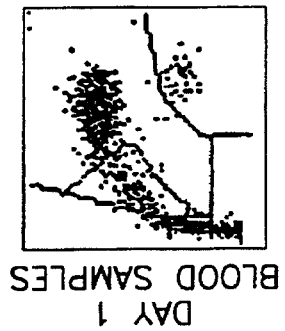
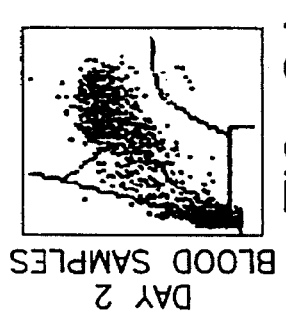
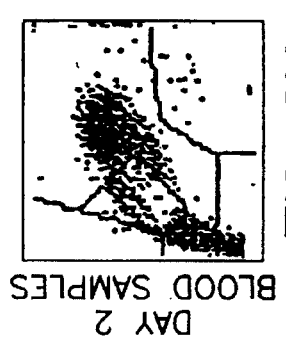
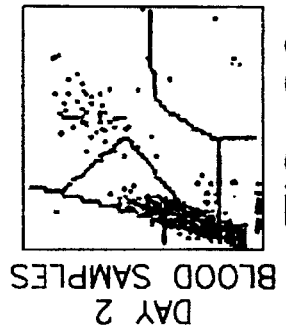
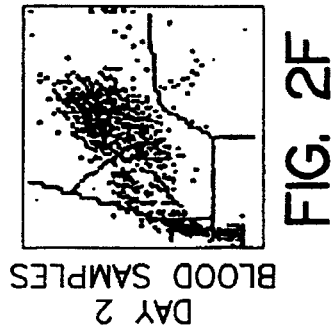

DAY 1 SAMPLE
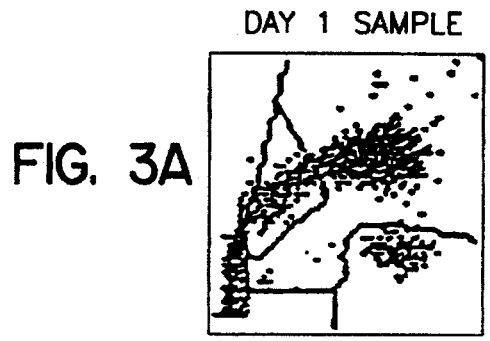
FIG. 3A
| Px R1 Reagent: | |
|---|---|
| Brij 35(g/L) + | 0.0 |
| SDS(g/L) | 0.105 |
| Rinse: | |
|---|---|
| Brij 35(g/L) + | 3.0 |
| SDS(g/L) | 2.0 |
DAY 1 SAMPLE
FIG. 3B
| Px R1 Reagent: | |
|---|---|
| Brij 35(g/L) + | 0.0 |
| SDS(g/L) | 0.105 |
| Rinse: | |
|---|---|
| Brij 35(g/L) + | 0.0 |
| SDS(g/L) | 2.0 |
DAY 2 SAMPLE
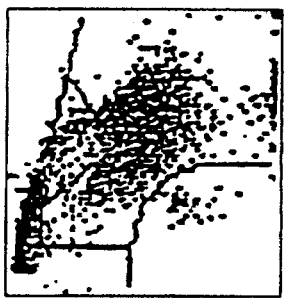
FIG. 3C
| Px R1 Reagent: | |
|---|---|
| Brij 35(g/L) + | 0.0 |
| SDS(g/L) | 0.105 |
| Rinse: | |
|---|---|
| Brij 35(g/L) + | 0.0 |
| SDS(g/L) | 2.0 |
| Pluronic P105 in PBS (g/L) | |
DAY 2 SAMPLE
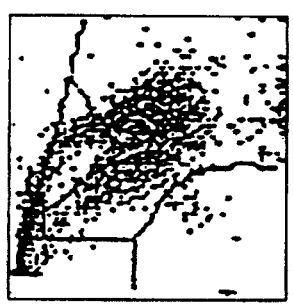
FIG. 3D
| Px R1 Reagent: | |
|---|---|
| Brij 35(g/L) + | 0.12 |
| SDS(g/L) | 0.105 |
| Rinse: | |
|---|---|
| Brij 35(g/L) + | 0.0 |
| SDS(g/L) | 0.0 |
| Pluronic P105 in PBS (g/L) | 1.0 |

Rinse: 2.0 g/L SDS

Rinse Carryover Volume (μL): 7.9

Rinse: 2.0 g/L SDS + 3.0 g/L Brij 35

Rinse Carryover Volume (μL): 7.9

Rinse: 2.0 g/L SDS

Rinse Carryover Volume (μL): 10.1

Rinse: 2.0 g/L SDS + 3.0 g/L Brij 35

Rinse Carryover Volume (μL): 10.1

Rinse: 2.0 g/L SDS

Rinse Carryover Volume (μL): 13.3

Rinse: 2.0 g/L SDS + 3.0 g/L Brij 35

Rinse Carryover Volume (μL): 13.3

METHOD AND REAGENT COMPOSITION FOR PERFORMING LEUKOCYTE DIFFERENTIAL COUNTS ON FRESH AND AGED WHOLE BLOOD SAMPLES, BASED ON INTRINSIC PEROXIDASE ACTIVITY OF LEUKOCYTES

FIELD OF THE INVENTION

The present invention relates to an improved leukocyte (i.e., white blood cell) differential method for whole blood samples and reagent compositions used in such a method. The leukocyte differentiation method and reagent compositions of the invention are based on the measurement of the intrinsic peroxidase activity of leukocytes. The method and compositions of the invention maintain the precision and accuracy of obtaining a leukocyte differential count on both fresh blood samples and on aged blood samples which have been stored at room temperature for about 48 hours, or in the cold, when the samples are analyzed electro-optically by light scatter and absorption flow cytometry.

BACKGROUND OF THE INVENTION

The five classes of white blood cells or leukocytes normally found in whole blood samples are neutrophils, lymphocytes, monocytes, eosinophils, and basophils. To determine the relative proportions of these five normal types of white blood cells, as well as to detect the presence and concentration of any abnormal cells in a whole blood sample, a medical diagnostic procedure is conventionally performed to examine a dried, stained smear of blood on a microscope slide. Such a procedure is referred to as a differential white blood cell count and is described in Miale, J. B., "Laboratory Medicine—Hematology", (1967), C. V. Mosby Company, St. Louis, Mo., pp. 822–830, 1126, 1127 and 1130. In addition to the above-listed five classes of leukocytes in blood samples, differential white blood cell counts also detect and measure large unstained cells ("LUCs"). LUCs represent a small fraction of white blood cells in normal blood samples and comprise such cell types as large lymphocytes, activated lymphocytes, plasma cells, blast cells, and peroxidase-negative monocytes, neutrophils, and eosinophils.

Semi- and fully-automated hematology processes and automated flow system apparatuses therefor have been developed to ease the burden of differential white blood cell counting and blood sample analyses, such as described in U.S. Pat. No. 3,741,875 to Ansley et al.; U.S. Pat. No. 4,099,917 to Kim; and U.S. Pat. Nos. 4,801,549 and 4,978,624 to Cremins et at. Such processes and systems use electro-optical and cytochemical procedures to specifically detect, identify, quantify, and label individual cell types. In addition, manual procedures for determining white blood cell differential counts are known in the art; for example, see Miale, J. B., "Laboratory Medicine—Hematology", (1967), C. V. Mosby Company, St. Louis, Mo.

U.S. Pat. No. 5,389,549 to Hamaguchi et at. describes methods and reagents used for classifying leukocytes, in which the methods involve the detection of changes in electrical impedance at high frequency or the differences in conductivity between particles and fluid medium, and the reagents require one or two component solutions which contain specific types of anionic and nonionic polyoxyethylene-based surfactants having 18–30 repeating oxyethylene units per molecule and which also contain hyper- or hypo-osmotic agents and solubilizing agents. The two component reagents require both a first liquid diluent fluid and a second lysing reagent fluid.

An earlier procedure for preparing a cell suspension for use in such systems comprised treating an uncoagulated blood sample with a surfactant for about 1.5 minutes to precondition the red blood cells for lysis; thereafter adding a fixative to the cells for about 1 minute while maintaining a neutral pH; and then incubating the mixture at about 58° C. to 60° C. for about 2 minutes to lyse the red blood cells and fix the white blood cells, as described in U.S. Pat. No. 4,099,917 to Kim.

U.S. Pat. Nos. 4,801,549 and 4,978,624 to Cremins et al. describe a method and reagent for the determination of a differential white blood cell count which is performed more rapidly, which lyses red blood cells in a whole blood sample without damaging the white blood cells, and which causes minimal extra-cellular precipitation or clumping of cells. Such precipitates or cell clumps generate ambiguities in the cell detection and recognition phase(s) of the procedure. The procedure (or "peroxidase method") described involves a mixture comprising peroxide (i.e., hydrogen peroxide) and a suitable chromogen to stain and differentiate particular cell types in the leukocyte class.

It is imperative in each of these processes that as many red blood cells as possible be lysed, since red blood cells outnumber white blood cells by about 1000-fold in normal blood. Because of this, even if one percent of the red blood cells remains unlysed, it is difficult to achieve an accurate and precise white blood cell differential count.

In the peroxidase method as disclosed in U.S. Pat. Nos. 4,801,549 and 4,978,624, red blood cells are lysed and white cells are crosslinked or "fixed" after a whole blood sample is mixed with a solution comprising only one surfactant, a fixative such as paraformaldehyde or formaldehyde, a sugar or sugar alcohol, and a buffer to maintain approximately neutral pH. Hydrogen peroxide and an electron donor chromogen, such as 4-chloro-1-naphthol, form a dark-purple-colored precipitate in the peroxidase-positive granules located in the cytoplasm of certain white cells, namely, neutrophils, eosinophils, and monocytes. The precipitate is an insoluble reaction product the formation of which is catalyzed by endogenous peroxidase enzymes in the intra-cellular granules. Differentiating the cell types is carded out by electro-optical analysis in which cell size and degree of staining are measured (i.e., forward angle scatter versus absorbance) on a cell-by-cell basis and plotted in a cytogram which is then analyzed to obtain both a total white cell count and differential count of the different types of white cells in the sample. In addition, the total white blood cell count can be obtained independently of the differential count.

Prior to the improvements and advantages afforded by the present invention, an alkaline peroxidase diluent had been described and particularly used in an alkaline peroxidase method of white blood cell classification carded out on a Technicon H6000™ automated analyzer system. The prior alkaline peroxidase diluent had major drawbacks, such as instability of the reagent components and a consequent short shelf and storage life. In addition, the user was required to prepare a homogeneous working solution of the alkaline peroxidase diluent in order to carry out the alkaline peroxidase method. This was accomplished by the user's having to mix together a solution containing a high level (i.e., 4.5%) of sodium dodecyl sulfate and a solution containing a high level (i.e., 30%) of Brij® 35, thereby resulting in a working alkaline peroxidase diluent having elevated concentrations of the two classes of surfactants. Such user preparation not only involved irritant diluent reagent components, but was also laborious, and had to be performed a number of times, because the resulting homogeneous working alkaline peroxidase diluent was stable for only one week. As will become clear, the instability, the short storage capacity, and the user-handling problems of the alkaline peroxidase diluent, as well as the commercial disadvantages related thereto, have been vastly improved upon and overcome by the present invention as described herein.

Also prior to the present invention, a major drawback which hampered the accuracy and reliability of cell separation and quantification methods, particularly the peroxidase method of leukocyte differential counting, was variable rinse carryover in the method. It is known that rinse carryover varies from system to system and from analysis to analysis. In particular, the accuracy and precision of leukocyte differential analyses based on the peroxidase reaction method frequently suffered from the effects of such variable rinse carryover in the method. Those skilled in the art have assumed that rinse carryover contributes only a volumetric dilution to the method and that rinse carryover plays no active or functional role in the reaction steps of the method. Indeed, until the inventive discovery of the present invention, the skilled practitioner did not realize that rinse carryover was more than a simple volumetric effect in blood sample analysis, and had no solution to the problems offered by the present invention and described herein.

In addition, there is a need in the art for improved reagents and methods for analyzing and extracting useful clinical information from both fresh (i.e., less than or equal to eight hours postdraw) blood samples and also aged blood samples that may have been stored for up to about 48 hours at room temperature. It is also necessary to develop the appropriate reagent solutions and compositions comprising components which will alleviate the newly-described problems generated by variable rinse carryover and will yield accurate and reliable results, especially, but not limited to, in the employment of electro-optical analysis of a variety of blood sample types, e.g., fresh whole blood samples, aged whole blood samples, abnormal whole blood samples (e.g., hospital or patient source), and normal whole blood samples (e.g., non-hospital or "healthy" donor source) stored in a variety of ways (e.g., in the cold or at room temperature). There is a further need in the art for reagent compositions that are very stable, have long shelf and storage lives (e.g., greater than one week), and require no user or customer preparation or handling prior to their use in carrying out leukocyte differential counting methods and obtaining results therefrom. It is also necessary to achieve and/or to maintain acceptable levels of noise at the origins of the resulting cytograms when carrying out differential counts on room temperature-stored or aged blood samples using automated analyzers.

SUMMARY OF THE INVENTION

The present invention provides an improved reagent composition and method for quantifying and differentiating leukocytes in both fresh and aged whole blood samples using electro-optical procedures and flow cytometry analysis.

It is an object of the present invention to provide an optimal, improved reagent composition and method for use in semi- and fully-automated systems to avoid the problems of carryover of unwanted reaction components from one method step to another, thus allowing for clean separation and quantification of cell types without unacceptable levels of origin noise and cellular contamination in the cytograms resulting from the method used to achieve a white blood cell differential count.

It is a further object of the invention to provide a rinse reagent solution that does not play any functional role in the reaction steps of the white blood cell differential method and which does not participate in the reaction chemistry of the method, with particular regard to the peroxidase method.

It is another object of the invention to provide an automated peroxidase method and reagent composition which yield precise and accurate results with a variety of blood sample types, e.g., aged and fresh blood samples, abnormal and normal blood samples, and samples stored in both the cold and at room temperature.

Yet another object of the invention is to provide an improved reagent composition for use in the peroxidase method of enumerating and distinguishing among white blood cell types in a whole blood sample by absorption flow cytometry.

Still another object of the invention is to provide an optimized and improved method and reagent composition for the rapid and efficient quantitative measurement of the white blood cell count and subpopulation differential of whole blood samples using endogenous peroxidase staining in conjunction with automated hematology analysis and flow cytometry.

Another object of the invention is to provide a reagent preparation which improves separation of the eosinophil subpopulation of cells in a white blood cell sample.

It is another object of the invention to provide balanced and stable reagent compositions for optimizing the reaction steps of the white cell differential counting method involving peroxidase staining of aged whole blood samples and for removing and preventing any negative effects of rinse carryover in the method.

Yet another object of the invention is to provide safe and stable reagent preparations and methods, wherein the reagent compositions are convenient and ready-to-use and require no additional preparation or mixing by the user or customer prior to use. The reagent compositions of the invention are stable and maintain long storage and shelf lives (e.g., greater than one week and at least about one year) at room temperature. A further object is to streamline the leukocyte differential counting method and to reduce the numbers of reagents that are needed for use in carrying out the steps of the method.

Further objects and advantages afforded by the invention will be apparent from the detailed description hereinbelow.

ABBREVIATIONS AND TERMS

The following abbreviations and terms are defined or explained for the convenience of those skilled in the art and are not intended to limit the scope of the invention in any way:

The lysis of red blood cells in the peroxidase method as performed on automated analyzers exemplified herein is defined by puncture of the cell membrane, causing most or all of the hemoglobin to leak out of the cell. The resulting red cell ghosts are capable of being chemically crosslinked or fixed by the fixative present in the composition of the peroxidase method. The red cell ghosts can be detected as noise in the origin region of a cytogram, which results from the electro-optical detection of cells in a sample using flow cytometry.

Peroxidase is abbreviated as "Px" throughout the instant specification.

As used herein, the terms aqueous reagent composition, reagent solution, and diluent are equivalent.

R1 is the first reaction phase of the Px method of white blood cell differential counting. As explained in greater detail herein, in the R1 phase of the Px method, a whole blood sample is mixed with a first aqueous reagent composition ("the Px R1 reagent composition" or "peroxidase R1 reagent composition") formulated in accordance with the invention. During the R1 phase of the Px method, all or most of the red blood cells in the sample are lysed and the white blood cells are chemically crosslinked or fixed by the fixative present in the R1 reagent composition.

Fresh blood samples are blood samples that are used for analysis less than or equal to eight hours postdraw. The term "fresh blood sample" is synonymous with the term "Day 1 sample" as used herein.

Aged blood samples are blood samples that have been stored at room temperature for up to about forty-eight hours postdraw. The term "aged blood sample" is considered to encompass the term "Day 2 blood sample" as used herein.

DESCRIPTION OF THE DRAWINGS

In the appended drawings of the figures, which are presented to further describe the invention and assist in its understanding through clarification of its various aspects, the figures depict cytograms obtained when the various aqueous reagent compositions or diluents or improved reagents thereof, prepared as described in accordance with the present invention, were utilized in the peroxidase method of determining differential white blood cell counts using the electro-optical detection apparatus of an automated hematology analyzer. The numerical labels as depicted in FIG. 1A serve to identify the different regions of the cytogram and are identical in each of the figures. As shown, number 1 indicates the area of the lymphocyte population; number 2 indicates the area of the monocyte population; number 3 indicates the area of the neutrophil population; number 4 indicates the area of the eosinophil population; number 5 indicates the area of origin noise arising from platelets and red cell ghosts; and number 6 indicates the area of the LUC population.

FIGS. 1A–1D represent the results of experiments performed to test whether the performance of the Px method of white blood cell differential counting using a peroxidase R1 reagent composition formulated to contain only ionic surfactant would yield acceptable results. The Px method further included a rinse cycle in which the rinse was formulated either without nonionic surfactant, or with the nonhemolytic surfactant Pluronic®. FIG. 1A is a cytogram depicting the results of the Px method performed on Day 1 blood samples. The R1 reagent composition used in FIG. 1A contained 0.105 g/L SDS (sodium dodecyl sulfate); the rinse reagent solution used in FIG. 1A contained 3.0 g/L of Brij® 35 and 2.0 g/L of SDS. FIG. 1B is a cytogram showing the results of the Px method performed on Day 2 blood samples. The R1 reagent composition used in FIG. 1B contained 0.105 g/L SDS; the rinse reagent solution used in FIG. 1B contained 3.0 g/L of Brij® 35 and 2.0 g/L of SDS. FIG. 1C is a cytogram showing the results of the Px method performed on Day 2 blood samples. The R1 reagent composition used in FIG. 1B contained 0.105 g/L SDS. In contrast to FIGS. 1A and 1B, the rinse reagent solution used in FIG. 1C contained 1.0 g/L of the nonhemolytic surfactant Pluronic® 105 in phosphate buffered saline (see Table 4). FIG. 1D is a cytogram showing the results of the Px method performed on Day 2 blood samples. Like FIG. 1C, the Px R1 reagent composition used in FIG. 1D contained SDS, but at a higher concentration, i.e., 0.17 g/L SDS. The rinse reagent solution was identical to that described for FIG. 1C. The FIG. 1A–1D results show that compared with acceptable results of the Day 1 blood sample analysis (FIG. 1A) carded out using an R1 reagent composition having only SDS and a rinse reagent having both the ionic surfactant SDS and the nonionic surfactant Brij® 35, the Day 2 blood sample analysis carded out using an R1 reagent composition formulated to contain only SDS and a rinse cycle solution the same as that used in FIG. 1A yielded acceptable origin noise. By contrast, if the rinse contained only Pluronic® P105 surfactant (FIGS. 1C and 1D), the cytograms showed unacceptable levels of origin noise. The FIGS. 1C and 1D reveal that ionic surfactant alone in the Px reagent composition is not sufficient to obtain acceptable and useful results from the Px method when the rinse does not contain nonionic surfactant such as Brij® 35. As determined by the present inventors, the unacceptable results of the analysis of the Day 2 blood samples shown in FIGS. 1C and 1D can be attributed to the lack of nonionic surfactant in the R1 reagent composition.

FIGS. 2A–2J represent the results of experiments performed to test whether the performance of the Px method using a Px R1 reagent composition formulated to contain only nonionic surfactant in varying concentrations would provide acceptable data and results. As shown, FIGS. 2A–2E are cytograms depicting the results of the Px method performed on Day 1 blood samples, and FIGS. 2F–2J are cytograms depicting the results of the Px method performed on Day 2 blood samples. The Px R1 reagent composition used in FIGS. 2A and 2F contained 0.12 g/L Brij® 35 and 0.105 g/L SDS and served as controls for the Day 1 and Day 2 blood sample analyses. The Px R1 test reagent compositions used in FIGS. 2B–2E and in FIGS. 2G–2J contained no ionic surfactant (i.e., 0.0 g/L SDS). These test reagent compositions contained the following amounts of the nonionic surfactant Brij® 35: FIGS. 2B and 2G contained 0.0 g/L of Brij® 35; FIGS. 2C and 2H contained 0.14 g/L of Brij® 35; FIGS. 2D and 2I contained 0.28 g/L of Brij® 35; and FIGS. 2E and 2J contained 0.42 g/L of Brij® 35. As shown in FIGS. 2A–2J, unacceptable cytograms result from the performance of the Px method using only nonionic surfactant in the Px R1 reagent composition. Thus, nonionic surfactant alone is not sufficient for obtaining acceptable results from the Px method.

FIGS. 3A–3D represent the results of experiments performed to test whether the performance of the Px method including a sample rinse cycle and using a Px R1 reagent composition formulated to contain both nonionic surfactant and ionic surfactant together would provide acceptable data and results, especially for analyses using Day 2 blood samples. As shown, FIGS. 3A and 3B are cytograms depicting the results of the Px method performed on Day 1 blood samples using a Px R1 reagent composition comprising 0.0 g/L of Brij® 35 and 0.105 g/L of SDS. The rinse solution used in the analysis shown in FIG. 3A comprised 3.0 g/L of Brij® 35 and 2.0 g/L of SDS. The rinse solution used in the analysis shown in FIG. 3B comprised 0.0 g/L of Brij® 35 and 2.0 g/L of SDS. FIG. 3C is a cytogram depicting the results of the Px method performed on Day 2 blood samples using a Px R1 reagent composition containing 0.0 g/L of Brij® 35 and 0.105 g/L of SDS, and a rinse cycle reagent comprising 0.0 g/L of Brij® 35 and 2.0 g/L of SDS. FIG. 3D is a cytogram depicting the performance results of the Px method using Day 2 blood samples, a Px R1 reagent composition comprising both 0.12 g/L of Brij® 35 and 0.105 g/L of SDS, and the newly-disclosed rinse reagent solution containing the nonhemolytic surfactant Pluronic P105 with neither SDS nor Brij® 35. The FIGS. 3A–3D results show that the integrity of the cytogram resulting from the analysis of Day 2 blood samples requires the inclusion of nonionic surfactant (e.g., Brij® 35) in addition to ionic surfactant in the R1 reagent composition when the rinse solution does not contain Brij® 35.

FIGS. 4A and 4B show the cytogram results of a rinse carryover volume of about 7.9 μL from the rinse cycle used in the Px method; FIGS. 4C and 4D show the cytogram results of a rinse carryover volume of about 10.1 μL from the rinse cycle used in the Px method; and FIGS. 4E and 4F show the cytogram results of a rinse carryover volume of about 13.3 μL from the rinse cycle used in the Px method. The cytograms demonstrate that the presence of the nonionic surfactant Brij® 35 in the rinse solution generates unacceptable results if the carryover volume exceeds about 8.0 μL.

DETAILED DESCRIPTION OF THE INVENTION

Figure 4A:
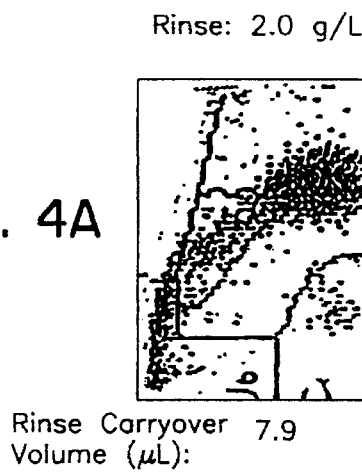
FIGS. 4A–4F are cytograms depicting results of experiments performed on whole blood samples to determine the effect of variable rinse carryover in the peroxidase method of the invention (see Example 5). The Px R1 reagent composition used in the experiments shown in FIGS. 4A–4F contained 0.105 g/L SDS. The compositions of the rinse solutions used in the rinse cycle differed such that the rinse contained either 2.0 g/L of SDS (as shown in FIGS. 4A, 4C, and 4E) or 2.0 g/L of SDS+3.0 g/L of Brij® 35 (as shown in FIGS. 4B, 4D, and 4F).

The present invention relates generally to improved methods and reagent compositions for the determination and quantification of white blood cell differential counts via a peroxidase (Px) method which relies on the measurement of the endogenous peroxidase activity of particular types of white blood cells. The invention relates particularly to semi-automated and automated flow cytometry analyzers and to improvements in the peroxidase method for white blood cell measurement and subpopulation determination.

To assist in the understanding of the present invention, a summary of the cellular and molecular events which occur in an automated peroxidase method of determining leukocyte differential counts is provided. In the first or R1 phase of the peroxidase method, a blood sample is mixed with an aqueous first reagent (R1) composition (i.e., an R1 solution or diluent), and the mixture is heated to about 70° C. for about 15–20 seconds. During this interval, the red blood cells lyse, their hemoglobin leaks out, and the resulting red cell ghosts are fixed. The white blood cells are chemically crosslinked or "fixed" by a fixative compound, such as formaldehyde, to provide resistance to lysis during the remainder of the reaction. In general, red blood cells are more easily lysed than are white blood cells and platelets; however, it is not uncommon for the red blood cell ghosts and platelets to become crosslinked under the conditions used during the procedure, because lysis and fixation are competing processes that occur in the same sample reaction mixture. Thus, the peroxidase method requires a fine balance between the lysis of red blood cells and the fixation of white blood cells in a blood sample. If the lytic strength of the Px R1 reagent composition is too great, both the red blood cells and the white blood cells will be damaged. Conversely, if the concentration of fixative is too great, all of the cells will be fixed before red cell lysis can occur. Nevertheless, a white blood cell differential count is attainable with high levels of accuracy and reliable determinations of cell types and cell numbers, especially in view of the speed and the optimum reaction conditions and reagent formulations for the improved peroxidase method as developed in accordance with the invention to perform rapid sample analyses that occur using semi- and fully-automated hematology systems.

In whole blood, the ratio of red blood cells to white blood cells is about 1000:1. Therefore, for optimal performance of the automated peroxidase method for whole blood sample analysis, it is clear that essentially all of the red cells should be lysed in the sample aliquot early in the analysis. Consequently, in the first reaction using the R1 diluent, there is a competition between lysis of red cells and crosslinking of white cells. If red cells survive the lysis step with intact hemoglobin, they will likely interfere in the differential count as they can erroneously be detected as lymphocytes because of placement in the lymphocyte area of the resulting cytogram. However, it is also crucial that the white blood cells in the blood sample aliquot are not attacked or degraded by solution components during the R1 phase of the peroxidase method.

During the second reaction phase (also called "reaction 2" or "R2" herein), which follows the R1 phase of the peroxidase method, the substrate solutions of hydrogen peroxide and an electron donor, such as 4-chloro-1-naphthol are added to the R1 reaction mixture. These compounds are substrates of endogenous cellular peroxidase, which is differentially present in those white blood cell types that "stain", including monocytes, neutrophils and eosinophils. Lymphocytes and large unstained cells (LUCs) do not contain endogenous peroxidase enzyme and, therefore, are not stained in the method. Combinations of red cell ghosts and platelets, which also do not contain endogenous peroxidase enzymes, are not stained and may contribute to origin noise, which is encountered and accommodated for in nearly every method involving whole blood cell analyses. Incompletely lysed red cells, which contain some or all of their hemoglobin, are detected in the lymphocyte region of the cytograms generated from the Px method, and interfere with the method. Platelets and platelet clumps are also detected in the lymphocyte region and are an additional source of interference.

In the peroxidase method, "staining" is the result of a complex chemical reaction in which the electron donor substrate such as 4-chloro-1-napthol is oxidized and polymerized into a deep purple reaction product which is trapped within the cells. Granules inside the cells stain purple, thereby allowing the cells to be observed in the peroxidase reaction mixture ("effluent") if examined under the microscope (stained cells look black to the naked eye using microscopic examination). On automated hematology analyzer systems, such as those exemplified by the H•™ systems commercially available under the trade designation TECHNICON H•1™, H•2™, H•3™, and the like, and sold by the assignee hereof, detection is made electro-optically by measuring light absorption (due to the purple reaction product) and light scatter (due to cell size).

The present invention provides a single new reagent composition for use in the R1 phase of the peroxidase method to improve and optimize the performance of the overall peroxidase method, as a result of the presence of a newly added component to the reagent composition; the component is a hemolytic, nonionic surfactant, e.g., Brij® 35. The presence of such a nonionic surfactant in conjunction with an ionic surfactant in the new reagent composition affords a novel Px 1 reagent or diluent which can be successfully used with the other reagents in subsequent reaction phases of the peroxidase method as outlined above. Those skilled in the art will appreciate that in the R1 phase of the Px method, the amount and concentration of surfactant is critical—i.e., too much surfactant can cause the white blood cells in the sample to be attacked and too little surfactant will not lyse the red blood cells in the appropriate manner and will thus contribute to high origin noise in the resulting cytograms.

In an embodiment of the invention, the new R1 reagent composition of the invention can also be used successfully when a rinse cycle employing an aqueous rinse reagent is also performed in the peroxidase method, provided that the rinse solution does not also contain a hemolytic nonionic surfactant such as Brij® 35. In particular, the R1 reagent composition of the invention can be used in conjunction with a new rinse reagent composition that is formulated to contain only a surfactant of the Pluronic® class, in the complete absence of other types of surfactants (i.e., without ionic surfactant, such as SDS, and without nonionic surfactant, such as Brij® 35).

The reagent composition of the invention solves the following problem which is further elucidated in the description and examples provided hereinbelow. It was determined by the present inventors in carrying out the peroxidase method as currently performed on automated analyzer systems, such as those exemplified by the above-mentioned H•™ systems, that there was routinely a volume of about 8 μL of rinse solution left over in the reaction chamber at the end of one sample cycle of the peroxidase method. This seemingly small amount of rinse carryover became part of the next sample cycle; it was simply assumed by those performing the method that this volume did not affect the method in any functional way.

However, it was newly found that when such rinse carryover exceeded a volume of about 10 μL, the performance of the peroxidase method deteriorated. It was also unexpectedly discovered by the present inventors that nonionic surfactant, e.g., Brij® 35, but not ionic surfactant, e.g., SDS, present in the rinse solution (and carded over into the R1 reagent), actually caused the deterioration of the method. Simply put, and as will be described further hereinbelow, the present inventors discovered that the Brij® 35-containing rinse conventionally used in the peroxidase method was "delivering" nonionic hemolytic surfactant to the R1 phase of the method, thus allowing the Brij® 35 to participate in the method in a functional, but undesirable, manner in the method. As a result of these findings, the present inventors discovered that the rinse used in the peroxidase method actually contributed a required component (i.e., nonionic surfactant such as Brij® 35) to the R1 phase of the Px method, and that when the volume of rinse carryover varied from system to system, the performance and results of the peroxidase method were adversely affected. In accordance with the development of the invention as described herein, the present inventors first recognized that rinse carryover was not merely an innocuous phenomenon associated with the performance of the peroxidase method.

This knowledge led the present inventors to design the abovementioned improved R1 reagent composition that contained both nonionic surfactant and ionic surfactant for use in the R1 phase of the peroxidase method. In addition, the present inventors further improved the method by removing nonionic surfactant such as Brij® 35 from the rinse solution which could also be employed in the method via a rinse cycle. In addition, a new rinse solution containing nonhemolytic, nonionic surfactant, e.g., Pluronic®, was found to be most suitable for use in conjunction with the new R1 reagent composition in the Px method. By removing the lytic nonionic surfactant from the rinse solution (or by using nonhemolytic Pluronic® as the sole surfactant in the rinse), and by formulating a new Px 1 reagent composition containing both a suitable nonionic surfactant and an ionic surfactant, the nonionic surfactant in the R1 reagent could optimally be delivered at a controlled rate in the Px method. Also, variation in rinse carryover volume cannot affect the results obtained from the new method. Consequently, in the improved R1 reagent and peroxidase method, the active nonionic surfactant component is present only in the reagent composition used in the R1 phase of the method where its functional activity is required for the lysis of red cells. Moreover, when a rinse is used in the method, the rinse composition minus Brij® 35 (or containing only nonhemolytic Pluronic® as the surfactant) is optimally devoid of any surfactant that can actively participate in the peroxidase method, so that unacceptable or unusable results caused by detrimental components of the rinse solution are alleviated.

The occurrence of rinse carryover and its associated problems in automated hematology methods are discussed further hereinbelow: in the analysis of whole blood samples using automated hematology analyzers, all of the blood samples analyzed are mixed with reagent solutions and flow through a common hydraulic path (e.g., a channel). The channel is cleaned or rinsed between each sample cycle by the introduction of a volume of rinse. In this process, the channel is never completely devoid of rinse solution or allowed to dry out. As a consequence of the rinsing process, some of the rinse solution is left behind and enters the next sample cycle. This describes the phenomenon of rinse carryover.

It is thus clear that rinse carryover may contribute variable amounts of reactive components from one sample cycle to the next sample cycle in some systems used to perform the peroxidase method. This is particularly evident when different systems are compared with each other. The system-to-system variation of rinse carryover volume can vary in both subtle and more pronounced levels to impact negatively on the results of the method performed on an automated analyzer. For example, in the latter case, more gross volumes of rinse carryover (e.g., greater than about 10 μL) cause poor results in the method. In the former case, even more subtle system-to-system variation in rinse carryover volumes (e.g., volumes such as 7.5 μL, 8.0 μL, 8.3 μL among different systems) causes each system to perform slightly differently. Until the invention as described, both of these kinds of rinse carryover volume variation adversely affected and caused problems in the existing peroxidase differential counting method.

As discussed above, prior to the present invention, it was formerly accepted by those in the art that variable rinse carryover was simply a benign volumetric carryover that occurred in performing the method. However, as demonstrated further herein, the present inventors discovered through quantitative measurement of carryover volumes and analysis of the reaction components and steps of the method, that rinse carryover (whether it occurred more subtly yet more insidiously in the form of limited, but different, volumes from system to system, or whether it occurred as a more dramatic volume change from system to system) contributed more than mere volumetric dilution to the method, caused deviations and flaws in the existing method, and impaired the performance of the method by playing an active role, rather than an inactive one, in the peroxidase method of leukocyte identification and quantification.

As a particular example, it was found that exceeding a particular level of active surfactant in the R1 phase of the method caused distortion of the resulting cytogram, which was characterized by damaged eosinophils that clustered and rose into the neutrophil area of the cytogram (FIGS. 4A–4F), as well as by poorly stained and irregular populations of neutrophils. Example 5 demonstrates that rinse solution carryover contributed a variable amount of the nonionic surfactant Brij® 35 to the R1 phase of the Px method (involving the lysis of red blood cells and the crosslinking of white blood cells).

Accordingly, the present invention succeeded in alleviating active participation by surfactant components of the rinse solution in the Px method by removing the surfactant components from the rinse, and also freed the method from the effects of variable rinse carryover. This was further achieved by devising new formulations of the Px R1 reagent composition, with an end result of having "active" surfactant components present only in the Px R1 reagent composition (where their delivery is controlled and constant in the R1 phase of the Px method) and not in the rinse solution (where the delivery of rinse reagent components via the sample rinse cycle is variable and less well controlled). Consequently, the invention yields accurate results as well as a constant concentration of the appropriate type of nonionic surfactant, e.g., Brij® 35, in the overall method.

Another goal of the development of the reagent composition and improved peroxidase method of the invention was to simplify the design of automated analyzer systems by reducing the number of different types of rinses that are currently used in carrying out the peroxidase method and other automated hematology analysis methods. If one rinse reagent was developed and was found to be compatible with many different blood analysis methods and automated systems, then system design would ultimately be simpler and more economical.

Although the simplest rinse composition could be formulated without a hemolytic, nonionic surfactant, such as Brij® 35, it was also found that merely any "Brij® 35-free" rinse solution was still not acceptable for use in the peroxidase method. For example, an aqueous rinse solution containing only SDS was determined to be unacceptable for use in the method because SDS is subject to crystallization at cold temperatures. This behavior of SDS would preclude its use and suitability in the aqueous rinse composition which must be able to be stored longterm with no adverse effects to its components or to their operativity in the rinse reagent composition or the rinse cycle of the method. Thus, it was necessary for an acceptable formulation of rinse reagent to be discovered and devised. Accordingly, one aspect of the present invention is the formulation of an aqueous rinse composition containing only the nonhemolytic surfactant Pluronic® for novel use in the Px method.

As detailed hereinbelow and in the examples, use of the improved, dual-surfactant-containing Px R1 reagent composition, as well as a suitable rinse solution when a rinse cycle was carried out, resulted in an improved peroxidase method that provided acceptable results when both fresh and aged blood samples were analyzed. In contrast, the current Px method performed using a conventional R1 reagent composition (i.e., formulated in the absence of nonionic surfactant, such as Brij® 35), resulted in unacceptable results in the form of high levels of origin noise when aged blood samples were analyzed. It is noted that the concentration of the nonionic surfactant used in the new Px R1 reagent composition approximates the concentration of the nonionic surfactant Brij® 35 that was discovered to be carded over into the R1 phase of the method due to rinse carryover in the current peroxidase method.

In accordance with the improved Px method of the invention, acceptable levels of origin noise in the cytograms of aged blood samples were found to be a function of including a suitable nonionic surfactant, e.g., Brij® 35, in the Px R1 reaction mixture (FIGS. 1A–1D and 3A–3D). Use of a rinse solution devoid of lytic surfactant (or containing an appropriate nonhemolytic surfactant, such as Pluronic®) was also found to achieve useful results from aged blood samples in the peroxidase method of leukocyte differential counting and to aid further in the ability to yield acceptable levels of origin noise.

The new R1 reagent composition achieves several advantages for the successful performance and results of the peroxidase method. For example, as mentioned above, the aqueous R1 reagent composition is formulated to contain both nonionic surfactant and ionic surfactant at concentrations sufficient to lyse red cells, but not to adversely affect the analysis of the white cell populations in the sample. The rinse solution for use in the improved leukocyte differential method preferably contains a nonhemolytic surfactant that is different from the surfactants that were discovered to improve the operativity of the novel R1 diluent of the improved peroxidase method. Using the R1 diluent reagent in combination with the above-described rinse reagent provides a peroxidase method that is independent of the effects of active surfactant transfer due to rinse carryover. Thus, although rinse carryover may not be completely removed or alleviated, the use of a rinse that is free of nonionic hemolytic surfactant (e.g., Brij® 35) eliminates the adverse or detrimental effects of rinse carryover and removes the intersystem variability due to rinse carryover in carrying out the method. Further, the novel reagent composition of the invention, formulated to contain two surfactants as described, showed success in maintaining the accuracy of the differential analysis, as well as achieving acceptable levels of origin noise when analyzing aged blood samples stored both at room temperature and in the cold for at least about 48 hours.

In accordance with the invention, the improved and novel R1 reagent composition, most preferably aqueous, includes two, lytic components which are different surfactant types: at least one nonionic surfactant such as a long chain alkyl ether polyethoxylate, e.g., the polyoxyethylene(2–20)lauryl, cetyl, myristyl, stearyl, and oleyl ethers, e.g., Brij® 35, formulated in combination with at least one ionic surfactant, preferably of the class of alkali metal salts of an alkyl sulfate having from about 10 to about 16 carbon atoms, e.g., sodium dodecyl sulfate (SDS). Suitable ionic surfactants for use in the Px R1 reagent composition also comprise those of the class of zwitterionic sulfobetaines with straight chain alkyl groups having from about 10 to about 16 carbon atoms, e.g., tetradecyldimethylammoniopropylsulfonate or TDAPS and or dodecyldimethylammoniopropanesulfonate or DDAPS. The combined action and appropriate concentrations of the surfactants formulated in the Px R1 reagent mixture of the invention result in the appropriate lysis of the red blood cells as described herein and the leakage and loss of the hemoglobin contents of the lysed red cells.

The improved Px reagent composition also comprises a fixative or crosslinking component (e.g., formaldehyde or paraformaldehyde), a sugar or sugar alcohol, a buffer or buffer mixture to maintain the pH of the reagent in a neutral or near neutral pH range, an inorganic salt or salts, and a chelator of polyvalent metal ions, if necessary or desired. All of the components of the improved reagent composition and method, including the temperature and reaction time in the R1 lytic phase of the reaction, are balanced and optimal for achieving improved results in the method. The improvements afforded by the present invention ameliorate the clinical usefulness of the results of the method.

This new, dual-surfactant-containing reagent composition used in the R1 phase of the peroxidase method is stable and has a long shelf life. For example, to test the long-term durability of the reagent composition, the new R1 reagent composition was prepared and stored for thirty days at 60° C. (i.e., under conditions of an accelerated stability test which indicates to those skilled in the art that the reagent will ultimately be stable for one year or more at room temperature (i.e., about 22°–30° C.)). When this "long-term" stored reagent was used in the peroxidase method as described, the results obtained were still acceptable and useful.

In developing and formulating the reagent composition of the invention, test reagents were prepared and assayed using both Day 1 and Day 2 blood samples, particularly those aged at room temperature. The chemical parameter used to evaluate the suitability of the nonionic surfactants, in particular, the polyethoxylates, in the R1 reagent composition of the invention is known as the hydrophilic lipophilic balance or HLB value (for HLB values and molecular formulae, see *Encyclopedia of Surfactants*, compiled by Michael and Irene Ash, Chemical Publishing Company, New York, N.Y., 1980; and *McCutcheon's Emulsifiers and Detergents*, McCutcheon Division, MC Publishing Company, Glen Rock, N.J., 1987). The surfactant properties of surfactants are correlated with the HLB value. Thus, in accordance with an aspect of the invention, the HLB value of a given surfactant serves as a useful predictor for whether or not that surfactant will be suitable as a component of the reagent composition of the invention. In particular, an appropriate HLB value as described hereinbelow indicates that a surfactant will function to improve results in the analysis and differential determination of whole blood samples that are at least about two days old and stored at room temperature.

In accordance with another aspect of the invention, a reagent composition formulated to contain a nonionic surfactant which possessed an HLB greater than about 17.3 to 17.5, indicative of too great a hydrophilicity, was unsuitable for improved performance of the method. HLB values of surfactants suitable for use in the reagent composition of the invention range from about 8.9 to about 17.5, preferably about 9.3 to about 17.3, and more preferably about 9.5 or 9.6 to about 16.9. Ideally, the surfactant in the reagent composition of the invention should be useful in an oil-in-water emulsification application, in which water-insoluble oils (i.e., lipids from cell membranes) are "dissolved" by the surfactant micelles which are present in the aqueous solvent. In aqueous solution, micelles have elliptical or spherical shapes and are groups of surfactant molecules (e.g., containing about 100 molecules) in which the polar groups face the water solvent and the hydrophobic core is in the interior (M. J. Rosen, 1978, "Surfactant and Interfacial Phenomena", Wiley and Sons Interscience Publications, New York, N.Y.). HLB values of from about 9.5 to about 17.5 are indicative of utility in such oil-in-water emulsifications. As mentioned above, HLB values greater than about 17.3 to 17.5 , and more particularly, 17.3, did not improve the performance of the method. Tables 9 and 10 present the results of the leukocyte differential method of the invention carried out using a variety of different nonionic surfactants on an automated analyzer (see Example 7). Similarly, surfactants having HLB values less than about 9.3 were also not generally useful in the method.

For the ionic surfactant class of alkali metal salts of an alkyl sulfate having from about 10 to about 16 carbon atoms, the preferred alkali metal cations for the R1 reagent composition of the invention are sodium, potassium, and lithium. More preferred are alkali metal dodecyl sulfates, with sodium dodecyl sulfate being most preferred. Examples of concentration ranges of the anionic surfactants suitable for use are from about 0.030 g/L to about 0.150 g/L, preferably about 0.050 g/L to about 0.125 g/L, and more preferably about 0.085 g/L to about 0.105 g/L. Also suitable for use are the anionic alkyl benzene sodium sulfonates having from about 10 to about 18 carbon atoms. Examples of other anionic surfactants that are suitable for use in the invention are the N-acyl-n-alkyltaurates (for example, R—C(O)N(R') $CH_2CH_2SO_3^-M^+$, where $R=C_{10}H_{23}$—$C_{14}H_{29}$; $R'=CH_3$ or H; and $M^+=Li^+$, $Na^+$, or $K^+$). Further, zwitterionic surfactants, such as members of the sulfobetaine family, which also includes the homologous $C_{16}$ and $C_{12}$ members, e.g., TDAPS (tetradecyldimethylammoniopropanesulfonate), are suitable for use in the invention (see Example 8). Other examples of zwitterionic surfactants which can be used in the invention are derivatives of cholic acid, such as CHAPSO (3-[(3-cholamidopropyl) dimethylammonio]-2hydroxy-1-propanesulfonate), and the alkyl N,N-dimethyl N-oxides having from about 12 to about 16 carbon atoms, also called the N-oxides. A particular but nonlimiting example of an N-oxide is lauryl dimethylamine N-oxide (LO), and the like. Surfactants similar to TDAPS, but having fewer carbon atoms, for example, $C_{12}$, e.g., DDAPS (N-dodecyl-N, N-dimethyl-3-ammonio-1-propanesulfonate), may also be used in the peroxidase method and reagent of the invention.

Families of nonionic surfactants that are suitable for use in the reagent composition of the invention are (1) polyoxyethylene alkyl or aryl ethers (also termed polyethoxylates), including straight-chain aliphatic hydrophobes etherified to polyethylene glycol or polyoxyethylene ethanol, e.g., Brij® 35; (2) branched-chain aliphatic/aromatic (e.g., octylphenol) hydrophobes etherified to polyethylene glycol, e.g., Triton X®-100; (3) straight-chain aliphatic/aromatic (e.g., n-nonylphenol) hydrophobes etherified to polyethylene glycol, e.g., Igepal® C0897; and (4) straight-chain aliphatic (e.g., carboxylic acid) hydrophobes esterified to polyethylene glycol, e.g., Myrj® 53. Of these four families, the ester type is subject to hydrolysis in aqueous solution and is expected to be somewhat less stable than the ether types of surfactants.

Examples of nonionic surfactants of the first family include, but are not necessarily limited to, polyoxyethylene (4) lauryl ether (Brij® 30); polyoxyethylene(23) lauryl ether (Brij® 35); polyoxyethylene(2) cetyl ether (Brij® 52); polyoxyethylene(20) cetyl ether (Brij® 58); polyoxyethylene(2) stearyl ether (Brij® 72); polyoxyethylene(10)stearyl ether (Brij® 76); polyoxyethylene(20) stearyl ether (Brij® 78); polyoxyethylene(2) oleyl ether (Brij® 92); polyoxyethylene (10) oleyl ether (Brij® 96); and polyoxyethylene(20) oleyl ether (Brij® 98); polyoxyethylene(21) stearyl ether (Brij® 721); polyoxyethylene(100) stearyl ether (Brij® 700). Of the Brij® surfactants, the most preferred is Brij® 35. It is noted that, although suitable for use in the composition of the invention, the polyoxyethylene oleyl ethers may be less stable for long-term storage, due to the presence of double bonds in their molecular structures, which makes them susceptible to oxidation. It will also be appreciated by those skilled in the art that the most suitable nonionic surfactants will have HLB values in the ranges described, in accordance with the invention. Other nonlimiting examples of nonionic surfactants of the second family include Triton X®-100 (non-reduced or reduced), Triton®X-114 non-reduced or reduced), Triton X®-165, and Triton X®-305 (non-reduced and reduced). The nonionic surfactant should be present in the reagent composition of the invention at a concentration of from about 0.10 g/L to about 0.20 g/L; more preferred is a concentration range from about 0.10 g/L to about 0.16 g/L; and most preferred is a concentration range of from about 0.12 g/L to about 0.14 g/L.

The sugar or sugar alcohol of the composition include sucrose, fructose, dextrose, sorbitol, and mannitol. Dextrose is the preferred sugar to be used in the reagent composition. However, sugar alcohols, such as sorbitol, are more preferred. Sugar alcohols provide for a more stable reagent solution over time, due to the inability of the sugar alcohol to be air-oxidized. The sugar or sugar alcohol is ideally present in the reagent composition at a concentration of about 110.0 g/L to about 120.0 g/L, more preferably at 113.0 g/L. If a sugar other than dextrose, or a sugar alcohol other than sorbitol is used, the amount used should be adjusted so that the alternative sugar or sugar alcohol is present at approximately the same concentration (g/L) as dextrose or sorbitol. The sugar or sugar alcohol is present in the reagent solution to increase the detectability of the lymphocytes over the noise (i.e., the red cell ghosts and platelets). Either a sugar or a sugar alcohol may be used, depending upon the nature and requisites of the analysis.

Formaldehyde or paraformaldehyde is used in the reagent solution of the invention as a fixative (i.e., chemical crosslinking compound) for the white blood cells. If formaldehyde is used, it is present in the solution in an amount of from about 50 g/L to about 60 g/L. More preferably, formaldehyde is present in a concentration of from about 52 g/L to about 58 g/L.

The increased stability of the reagent solution when a sugar alcohol is used rather than a reducing sugar like glucose relates to the phenomenon of air-oxidation of glucose (but not a sugar alcohol) over time to form gluconic acid. See, for example, Nishikido et al., Jap. Kokai Tokyo Koho 80 40, 606, *Chem. Abs.*, 93:22120d, (1950) and U.S. Pat. No. 4,801,549. The presence of gluconic acid lowers the pH of the solution. When the pH falls outside of the range of the invention, as discussed herein, the method is subject to interference due to the non-lysis of red blood cells in the sample. Further, a sugar alcohol which cannot be air-oxidized, may chemically combine with formaldehyde to form a polyacetal, thereby preventing the oxidation of formaldehyde to formic acid, which, if produced, would also lower the pH of the reagent solution (U.S. Pat. No. 4,801,549).

An inorganic salt may also be included in the reagent solution. Salts suitable for use in the present invention may be alkali metal chloride salts such as NaCl, KCl and LiCl. Sodium chloride, NaCl, is a preferred salt. Such salt may optionally be present because it may aid in discriminating the neutrophils from the eosinophils by causing a difference in peroxidase stain intensity using light scatter/absorption optics. Other halogen salts (i.e., fluoride, bromide and iodide) over-inhibit peroxidase activity of the neutrophils, thereby preventing the discrimination of neutrophils from the other unstained white blood cells (WBCs). The salt, e.g., NaCl, when used, should preferably be present in an amount of from about 6.8 mM to about 10.3 mM (or about 0.4 g/L to about 0.6 g/L).

The buffer or mixture of buffers useful in this invention should be those suitable for maintaining the pH of the reagent solution at from about 6.8 to about 8.0, preferably from about 6.9 to about 7.6, more preferably about 7.0 to about 7.3. It is noted that when the pH is too low, i.e., below about 6.8, red blood cell interference is observed in cytograms. Suitable buffers include sodium or potassium phosphates, diethyl malonate, 3-(N-morpholino) propane sulfonic acid, (MOPS), N-2-acetamido-2-aminoethane sulfonic acid (ACES), and 4-(2-hydroxyethyl)-1-piperazine-ethanesulfonic acid (HEPES). Preferred is a mixture of $Na_2HPO_4$ (sodium phosphate, monobasic) and $NaH_2PO_4$ (sodium phosphate, dibasic). As indicated, the buffers should be present in the reagent solution of this invention in an amount suitable to maintain the pH of the solution at approximately neutral levels. For instance, when a mixture of $Na_2HPO_4$ and $NaH_2PO_4$ is used, the mixture should contain a mole ratio of $Na_2HPO_4$ to $NaH_2PO_4$ which is from about 2.04:1 to about 0.81:1 to produce a series of solutions with a pH range of about 6.9 to about 7.6, preferably from about 7.0 to 7.3. The buffer concentration of such mixture in the reagent solution of this invention is from about 75 mM to about 125 mM. Above about 125 mM may cause red blood cell interference in the resulting cytograms.

The reagent solution useful in the practice of this invention is an aqueous solution and, preferably, deionized water is used. The solution is prepared by combining the ingredients, in admixture, in water. A close watch should be maintained on the pH of the solution to ensure that it stays within the desired range. Those skilled in the art may also include other additives in the reagent solution as desired. In particular, metal chelators, such as disodium or trisodium ethylenediamine tetraacetic acid (EDTA) and ethylenebis (oxyethylenenitrilo)-tetraacetic acid (EGTA) are valuable to include in the reagent composition at a concentration of about 1 mM to about 5 mM to protect other components in the composition from polyvalent metal ion-catalyzed autooxidation. In addition to EDTA, disodium, trisodium, and tetrasodium EDTA or EGTA are suitable for use in the composition, with disodium EDTA, dihydrate being preferred. For instance, formaldehyde, sorbitol, SDS, and Brij® 35 are all susceptible to autooxidation. Polyvalent metal ion catalysts, e.g., $Cu^{+2}$ and $Fe^{+3}$, are frequently present in ppb concentrations in water which is used as the formulation solvent ("Polymer Stabilization", 1972, Ed., W. L. Hawkins, Wiley-Interscience, New York, N.Y.).

A common pattern characteristic of unsuitable reagent compositions for use in the R1 phase of the peroxidase method is exemplified by the following: percent origin noise greater than 33; artificially elevated white blood cell count; and distorted percent neutrophils and percent lymphocytes. Based on the testing of many reagent formulations containing a variety of surfactant types and evaluating their performances on both fresh and aged blood samples, suitable components of the improved reagent composition and method of the invention were determined.

Table 1 provides an example of the preferred components and optimal concentrations and concentration ranges in the dual surfactant-containing aqueous reagent composition of the invention. It will be appreciated by those in the art that the concentrations and ranges of each of the listed reagent components may deviate by about ±5% to 10% without adversely affecting the composition or its use in the method. In addition, for each of the components of the new Px R1 reagent composition as listed in Table 1, the preferred quantities per liter are provided in parentheses, and are not intended to be limiting.

TABLE 1

| Component | Qty/L |
| --- | --- |
| Nonionic surfactant (e.g., Brij ® 35) | 0.10 g–0.20 g (0.12–0.14 g) |
| Ionic surfactant (e.g., Sodium Dodecyl Sulfate, SDS or TDAPS) | 0.085 g–0.115 g (0.105 g) |
| Sugar or Sugar alcohol (e.g., Sorbitol) | 110 g–120 g (113.0 g) |
| NaPhosphate, monobasic | 1.98 g–2.18 g (2.08 g) |
| NaPhosphate, dibasic | 11.30 g–12.5 g (11.89 g) |
| Inorganic salt (e.g., NaCl, KCl, LiCl) | 0.4 g–0.6 g (0.488 g) |
| Metal ion chelator (e.g., EDTA; EFTA; or di, tri, or tetrasodium EDTA or EGTA) | 0.675 g–0.825 g (0.750 g) |
| Fixative (e.g., formaldehyde, 37 g/dL) | 50 g–60 g (150 mL) |
| Deionized Water, q.s. to | 1.00 L |
| pH | 6.9–7.6 (7.0–7.5) |

Another aspect of the invention relates to a further improvement of the analytical results of the peroxidase method as a consequence of the incorporation of a rinse cycle and the use of an appropriate aqueous rinse reagent composition in the method. The rinse reagent employed in the rinse cycle of the improved method is especially advantageous and useful in semi- and fully-automated systems, in particular, the TECHNICON H•1™, H•2™, and H•3™ systems, and the like, which rapidly perform the peroxidase method of white blood cell differential counting. The rinse reagent is the subject of the invention described in co-pending U.S. application Ser. No. 08/443,363, filed concurrently herewith on May 16, 1995, entitled "Universal Rinse Reagent Composition For Use in Hematological Analyses of Whole Blood Samples", and assigned to the assignee of the present invention.

The rinse reagent solution, which can be used in the improved leukocyte differential counting method, comprises one or more buffering agents or compounds or mixtures thereof, for example, monobasic sodium phosphate and dibasic sodium phosphate, to provide a pH and an osmolality which are close to physiological values, e.g., pH of about 6.9 to about 7.6, and preferably a pH of about 7.0 to about 7.1, and an osmolality value of approximately 300 mOsmol/kg; an antimicrobial compound to retard microbial growth; a non-hemolytic surfactant, such as the Pluronics®, for example, P84, P85, P103, P104, P105, and P123 (P105 is preferred due to its nonlytic properties in the amounts used in the rinse solution, has a molecular weight of about 3300, and comprises about 50% polyoxyethylene, by weight); an alkali metal chloride salt, such as NaCl, KCl, LiCl, and the like. Nonlimiting examples of suitable antimicrobials include Proclin 150 (2-methyl-4-isothiazolin-3-one) and Proclin 300 (5-chloro-2-methyl-4-isothiazolin-3-one) (Rohm & Haas); Germall 115 (N,N'-methylenebis[N'-(1-(hydroxymethyl)-2,5-dioxo-4-imidazolidinyl]urea) (Sutton Laboratories); Dowacil 200 (1-(3-chloroallyl)-3,5,7-triaza-1-azoniaadamantane chloride) (Dow Chemical); and Bronopol (Angus Chemical Company). Proclin 150 is preferred for use in the rinse composition.

A water-soluble antioxidant compound, for example, 3,3'-thiodiproprionic acid; 3,3'-dithioacetic acid; Trolox® (i.e., water-soluble vitamin E, Hoffman-LaRoche); BHT, butylated hydroxytoluene or (2, 6-di-tert-butyl-4-methylphenol); BHA, butylated hydroxyanisole or (2-tert-butyl-4-methoxyphenol; and MEHQ (p-methoxyphenol); or mixtures thereof, may also be used for stabilization of the nonhemolytic surfactant in the rinse reagent composition. 3,3'-thiodiproprionic acid is preferred for use in the composition. The final osmolality of the rinse solution is from about 285 mOsm/kg to about 305 mOsm/kg.

In its simplest formulation, the rinse reagent may comprise a phosphate buffer (e.g., phosphate buffered saline, pH of about 6.8 to 7.8) and a nonionic and nonhemolytic surfactant of the Pluronic® family or class of surfactants. Pluronics® are block copolymers of polyoxyethylene and polyoxypropylene of the structure: $(EO)_x$-$(PO)_y$-$(EO)_x$ (see Pluronic® & Tetronic® Surfactants, BASF Corporation, Parsippany, N.J., 1987) and are formed by synthesizing the polypropylene glycol unit, $(PO)_y$, by controlled polymerization of propylene oxide. Since Pluronics® can vary from about 950 to about 14000 g/mol in molecular weight, and (PO) can comprise from about 10 to 90% by weight, then "y" can range from about 1 to 133 units. Next, EO polymeric chains are formed on both sides of the poly(PO) unit to yield the Pluronic® copolymer. Those in the art are aware that EO polymerization can be controlled symetrically so that "x" is the essentially the same on each side or end of the Pluronic® molecule. Nonlimiting examples of the "x" and "y" values for the Pluronics® suitable for use in the universal rinse composition are as follows: "x" is about 1 to 36 units, more preferably about 17 to 37, and "y" is preferably about 14 to 48 units.

Pluronics® suitable for use in the rinse reagent have % EO values, by weight, in the range of about 10 to 80% by weight, with a molecular weight range from about 2000 to about 8000 g/mol. More preferred is a % EO in the range of about 30 to 70% by weight, with a molecular weight range from about 3000 to about 3600. For example, Pluronic® P105 and P85 have % EO values of about 50%, by weight, and Pluronic® P104 and P84 have % EO values of about 40%, by weight.

Table 2 sets forth an exemplary formulation of the rinse reagent that may be used to further improve the peroxidase method and includes the preferred amounts of each component to yield the appropriate and operative pH and osmolality of the final reagent solution. It will be appreciated by those in the art that the concentrations and ranges of each of the listed rinse solution components may deviate by about ±5% to 10% without adversely affecting the composition or its use in the improved method. In addition, as mentioned above, for each of the components of the rinse reagent composition as listed in Table 2, the preferred quantities per liter are provided in parenthesis, and are not intended to be limiting.

TABLE 2

| Component | Qty/L |
| --- | --- |
| Antimicrobial compound (e.g., Proclin 150) | 0.25 mL–0.60 mL (0.40 mL) |
| Nonhemolytic nonionic surfactant (e.g., Pluronic ® P105) | 0.50 g–1.5 g (1.00 g) |
| NaPhosphate, monobasic | 0.285 g–0.315 g (0.300 g) |
| NaPhosphate, dibasic | 2.28 g–2.52 g (2.40 g) |
| Inorganic salt (e.g., NaCl, KCl, or LiCl) | 7.40 g–8.0 g (7.70 g) |
| Antioxidant compound (e.g., 3,3'-thiodiproprionic Acid) | 0.050 g–0.150 g (0.100 g) |
| Deionized water, q.s. to | 1.00 L |

TABLE 2-continued

| Component | Qty/L |
| --- | --- |
| pH | 6.9–7.5 |
|  | (7.0–7.3) |
| Osmolality (mOsmol/kg) | ≈285–305 mOsm |
|  | (300 mOsm) |

A significant advantage of the improved reagent in the Px method which also utilizes a rinse cycle is that the reagent composition of the invention is designed and optimized to eliminate the adverse effects attributable to variable rinse carryover in which the surfactant component of the rinse plays an undesirable and unacceptable functional role in the method. The reagent formulation and method also permit the determination of white blood cell differentials using aged blood samples that have been stored for up to two days at room temperature, without sacrificing accuracy, precision, and reliability of results due to unacceptable origin noise. Also, employing the reagent composition formulated in accordance with the invention in combination with the rinse solution formulation in accordance with the invention, the rinse solution does not participate in the peroxidase chemistry of the differential counting method.

In practicing the method encompassed by this invention, the reagent solution is rapidly mixed with the sample to be analyzed to form the reaction mixture in the R1 phase of the method. Uniform mixture should occur within about 5 seconds of the time the reagent solution and the blood sample come into contact with each other. If the two are not mixed rapidly and uniformly, a nonuniform level of fixation of the red blood cells may occur which prevents lysis of the red blood cells, thereby greatly impairing the accuracy of the differential WBC count obtained from the practice of the method.

When mixed, the reagent solution and the blood sample are slightly warmer than room temperature (e.g., about 5° C.). The reaction mixture (including the blood sample) is then rapidly heated to a temperature of from about 62° C. to about 76° C., ideally from about 70° C. to about 75° C., preferably by injection into the appropriate chamber(s) of an automated hematology analyzer maintained at a suitably elevated temperature. The heating of the reaction mixture should take place within about 15 seconds, preferably within about 20 seconds, otherwise red blood cell fixation can occur; fixed red cells will not be lysed and will be erroneously detected as lymphocytes, thereby interfering with the accuracy of the differential WBC count.

Immediately thereafter, a staining mixture comprising hydrogen peroxide and a suitable chromogen such as 4-chloro-1-naphthol is mixed with the reaction mixture. The initial temperature of the staining mixture may be room temperature and, ideally but not necessarily, the temperature after mixing the staining mixture with the reaction mixture is increased to from about 62° C. to about 72° C., preferably from about 65° C. to about 70° C. in a period of within about 30 seconds, preferably from about 8 to 15 seconds, in order to stain the neutrophils, monocytes, and eosinophils which are peroxidase active.

In practice, the reaction may proceed as follows: an automated hematology analyzer reaction chamber is maintained at a temperature of approximately 72° C. 12.0 µL of whole blood and 250 µL of the R1 reagent composition of the present invention are simultaneously injected into the system at room temperature, thereby rapidly mixing the two to form the reaction mixture, which is then incubated for up to less than about 30 seconds, preferably about 16 seconds, during which time the temperature of the mixture is increased to from about 62° C. to about 72° C. At the end of the incubation period, the red blood cells are optimally lysed and the white blood cells are fixed (i.e., crosslinked).

Immediately thereafter, 125 µL of a chromogen mixture (for example, 70 g/L of 4-chloro-1-naphthol in oxydiethanol) is simultaneously injected with 250 µL of a hydrogen peroxide solution comprising 3.0 g/L hydrogen peroxide. Both reagents are initially at room temperature, but due to the temperature of the reaction chamber, the staining mixture temperature is increased to from about 63° C. to about 69° C. within about 30 seconds, at which time the peroxidase staining of neutrophils and eosinophils is completed. The reaction chambers and system hardware are rinsed with the disclosed rinse solution to alleviate carryover of reagents and solutions from one sample analysis cycle to the next and to avoid skewed results due to the presence of contaminating reagents in the reaction chambers. Further particulars relating to the automated reaction procedure are described in Example 6.

Although the reagent compositions and procedure of the subject invention are illustrated using automated equipment, it will be readily apparent to those skilled in the art that the subject matter of the invention may also be applicable to manual methods and to manual methods in combination with semi-automated or fully-automated methods. Further, the reagent compositions and procedures of the invention have been illustrated using whole blood to arrive at the differential WBC count therein. It will be appreciated by those skilled in the art that the invention may also be employed with stock calibrator, control, and other solutions of blood cells which are specifically prepared and may be commercially available to calibrate and maintain apparatus accuracy. The term "sample" without other modifiers as used herein is specifically intended to include either whole blood or other solutions which contain blood cells.

EXAMPLES

The following examples are illustrative of the invention. They are presented to further facilitate an understanding of the inventive concepts and in no way are to be interpreted as limiting the present invention.

Example 1

Formulation and testing of a peroxidase R1 diluent reagent composition containing only ionic surfactant without nonionic surfactant (e.g., SDS alone, no Brij® 35)

Experiments were designed and carded out to determine the optimum formulation for the peroxidase diluent solution for use in the R1 phase of the peroxidase method.

The initial approach in formulating an acceptable and operative R1 composition or diluent involved the preparation and testing of reagent solutions containing ionic surfactant, i.e., the anionic surfactant SDS, in the absence of nonionic surfactant, i.e., Brij® 35, in the reagent composition. R1 reagent solutions were prepared based on increasing the SDS concentration from about 0.105 g/L to about 0.17 to 0.20 g/L. Several studies were completed to assay the performance of these "test" reagents containing high levels of SDS on automated systems at throughputs of 102 and 120 samples/hour.

Specifically, using an automated hematology analyzer, test R1 reagent solutions which contained from 0.16 to 0.20 g/L of SDS (e.g., 0.16, 0.17, 0.18, 0.19, and 0.20 g/L) were prepared and tested on Day 1 and Day 2 blood samples as indicated. The SDS test R1 diluents contained no Brij® 35 (e.g., 0.0 g/L). It is noted that the blood samples used in these experimental analyses were collected in Vacutainer™ tubes in the presence of $K_3$EDTA. In addition, in conducting these tests, the rinse solution used in the rinse cycle contained no Brij® 35. Rinse solutions were also used which contained the non-hemolytic surfactant Pluronic® P105, as described. The results of these analyses are presented in Table 3, which demonstrates that for Day 2 blood samples, unacceptable results were obtained with all of the test reagents. The data for the % neutrophils and % lymphocytes parameters are presented and compared with a standard method in which the rinse solution contained Brij® 35 at a concentration of 3.0 g/L and SDS at a concentration of 2.0 g/L. For the Day 2 blood samples, the recovery of these two parameters approached the standard at 0.20 g/L of SDS. However, using SDS at concentrations of between 0.16–0.19 g/L, the accuracy was poor due to unacceptable origin noise in the Px method. The wide disparity between replicate aspirations for particular samples is noted.

As shown in FIGS. 1A–1D, when Day 1 blood samples were analyzed in the peroxidase method using a standard peroxidase reagent solution comprising SDS (0.105 g/L) and no Brij® 35, and including a rinse cycle employing a rinse solution comprising Brij® 35 at a concentration of 3.0 g/L and SDS at a concentration of 2.0 g/L, the cytogram results showed nondiffuse, cleanly separated cell populations and minimal origin noise (see FIG. 1A). FIG. 1B shows the results of the analysis of Day 2 blood samples using the same Px R1 reagent solution and rinse solution as described for the FIG. 1A results. However, in contrast to the FIG. 1A results, the cytograms of the Day 2 blood samples showed diffusion of cell populations and higher origin noise. FIG. 1C shows the results of an analysis of Day 2 blood samples using an R1 test reagent solution containing only ionic surfactant in the form of 0.105 g/L of SDS, and including a rinse cycle employing a rinse reagent solution containing the non-hemolytic surfactant Pluronic® P105 in phosphate buffered saline (in the absence of both Brij® 35 and SDS). The results of the FIG. 1C cytogram show unacceptable noise at the origin. The same problem of unacceptable origin noise also resulted using a test reagent solution containing a higher amount of ionic surfactant (i.e., 0.17 g/L of SDS) and no Brij® to analyze Day 2 blood samples (see FIG. 1D), and using the same rinse solution described for FIG. 1C. Thus, it was determined that a peroxidase R1 composition containing only ionic surfactant (e.g., the anionic surfactant SDS) was suboptimal to use in the leukocyte differential method as described in conjunction with a "Brij®-free" rinse.

TABLE 3

| | Standard Method | | % Neut and % Lymph in Blood Samples Tested on Day 1 and | | | | | | | | | | | |
| | Reference | Reference | Day 2 (i.e., Aged and Stored at Room Temperature) | | | | | | | | | | | |
| Samp. | Day 1, Std† | | Day 2, Std | | Day 2*, 0.16** | | Day 2, 0.17 | | Day 2, 0.18 | | Day 2, 0.19 | | Day 2, 0.20 | |
| No. | % N | % L | % N | % L | % N | % L | % N | % L | % N | % L | % N | % L | % N | % L |
| 1a | 61.0 | 31.6 | 58.6 | 30.8 | 49.8 | 41.6 | 51.3 | 39.5 | 54.4 | 35.0 | 57.6 | 32.6 | 57.9 | 31.8 |
| 1b | 57.1 | 31.1 | 58.5 | 30.5 | 48.6 | 43.3 | 51.1 | 39.3 | 52.5 | 38.7 | 56.0 | 34.0 | 59.8 | 30.7 |
| 2a | 69.0 | 19.4 | 68.5 | 19.1 | 71.2 | 20.1 | 72.0 | 18.8 | 73.0 | 14.8 | 68.3 | 22.1 | 67.9 | 21.7 |
| 2b | 69.3 | 19.5 | 69.7 | 19.3 | 72.5 | 18.1 | 69.1 | 19.5 | 73.2 | 14.2 | 73.0 | 17.5 | 74.6 | 14.9 |
| 3a | 59.4 | 26.4 | 61.3 | 25.2 | 49.9 | 40.8 | 53.9 | 35.9 | 59.9 | 28.5 | 60.4 | 28.5 | 63.8 | 25.6 |
| 3b | 59.8 | 26.5 | 62.4 | 26.2 | 54.6 | 35.2 | 57.2 | 30.7 | 59.1 | 30.0 | 58.8 | 29.6 | 60.7 | 26.5 |
| 4a | 60.8 | 29.4 | 60.9 | 28.6 | 46.7 | 43.7 | 50.7 | 41.6 | 50.4 | 39.2 | 59.4 | 33.0 | 58.4 | 31.4 |
| 4b | 60.2 | 28.8 | 60.8 | 29.1 | 38.2 | 53.0 | 48.1 | 41.9 | 53.4 | 38.1 | 57.3 | 34.0 | 53.8 | 35.9 |
| 5a | 58.8 | 27.9 | 60.9 | 26.8 | 46.9 | 43.8 | 56.0 | 34.4 | 52.2 | 35.8 | 56.1 | 34.2 | 59.3 | 29.3 |
| 5b | 59.5 | 28.0 | 61.4 | 25.5 | 46.6 | 43.3 | 52.5 | 37.2 | 54.9 | 33.9 | 56.4 | 33.9 | 61.2 | 28.1 |
| 6a | 64.1 | 26.0 | 64.0 | 26.1 | 57.0 | 34.1 | 60.5 | 31.2 | 61.0 | 29.0 | 65.0 | 24.7 | 62.3 | 27.3 |
| 6b | 62.0 | 25.8 | 64.5 | 24.8 | 53.5 | 39.8 | 58.8 | 30.2 | 59.1 | 32.5 | 61.4 | 29.0 | 60.0 | 30.7 |
| 7a | 61.4 | 25.4 | 61.6 | 26.0 | 38.6 | 51.6 | 70.9 | 15.2 | 44.4 | 43.7 | 54.2 | 35.3 | 57.4 | 32.0 |
| 7b | 60.2 | 26.2 | 61.9 | 25.0 | 65.1 | 15.6 | 45.7 | 44.9 | 67.8 | 14.4 | 57.0 | 31.1 | 56.6 | 31.4 |
| 8a | 59.8 | 26.5 | 64.0 | 24.9 | 43.2 | 48.1 | 48.5 | 43.2 | 54.5 | 35.4 | 52.1 | 39.4 | 58.4 | 30.9 |
| 8b | 60.4 | 26.9 | 64.6 | 25.2 | 41.6 | 49.8 | 46.0 | 44.2 | 51.1 | 40.3 | 53.8 | 37.2 | 58.0 | 30.6 |
| 9a | 58.2 | 28.5 | 59.7 | 29.6 | 68.9 | 18.8 | 51.6 | 0.6 | 62.3 | 26.0 | 58.4 | 31.1 | 55.3 | 35.9 |
| 9b | 60.1 | 28.4 | 58.2 | 29.8 | 65.6 | 21.0 | 52.8 | 37.6 | 52.8 | 35.8 | 55.6 | 30.3 | 58.9 | 31.0 |
| 10a | 59.3 | 27.1 | 64.7 | 25.3 | 54.5 | 35.8 | 58.1 | 33.3 | 58.5 | 32.0 | 63.7 | 27.2 | 60.6 | 30.7 |
| 10b | 59.0 | 26.3 | 61.3 | 26.7 | 49.8 | 41.0 | 58.5 | 32.6 | 60.8 | 30.8 | 61.3 | 28.8 | 61.6 | 27.6 |
| mean | 61.0 | 26.8 | 62.4 | 26.2 | 53.1 | 36.9 | 55.7 | 32.6 | 57.8 | 31.4 | 59.3 | 30.7 | 60.3 | 29.2 |

% N: percent neutrophils in sample; % L: percent lymphocytes in sample.
† Std signifies a standard of control R1 diluent containing 0.105 g/L of SDS and no nonionic surfactant, and a rinse cycle and solution containing 3.0 g/L of Brij ® 35 and 2.0 g/L of SDS.
*Day 2 signifies that blood samples were assayed following about 36–48 hours at room temperature.
**0.16, 0.17, 0.18, 0.19, and 0.20 are the concentration of SDS in g/L present in the test peroxidase R1 reagent solutions. The rinse contained 1.0 g/L of Pluronic ® P105 in phosphate buffered saline (PBS).
The sample set was 10 non-hospital bloods, assayed in duplicate. Virgin tubes from the same set of donors were stored for 24 hours at room temperature and than assayed as the Day 2 samples.

Example 2

Formulation and testing of a peroxidase R1 diluent reagent composition containing only nonionic surfactant and no ionic surfactant (e.g., only Brij® 35 and no SDS)

In addition to the test R1 diluent compositions formulated to contain SDS alone, in the absence of nonionic surfactant, as described in Example 1, reagent compositions were also designed to test the presence of nonionic surfactant, i.e., Brij® 35, alone, in the absence of ionic surfactant, e.g., the anionic surfactant SDS. Accordingly, several test R1 diluent reagent compositions which contained Brij® 35 at concentrations of 0.0 g/L, 0.14 g/L, 0.28 g/L, and 0.42 g/L were prepared and assayed. For the test analyses using only Brij® 35 in the R1 diluent solution, the rinse solution used in the rinse cycle contained the non-hemolytic surfactant Pluronic® P105 as used in the assays described in Example 1.

The various Brij® 35-containing R1 test solutions were formulated as follows: a 30.0 g/L stock solution of Brij® 35 was prepared in distilled water. To 50 mL aliquots of the peroxidase R1 composition (without nonionic surfactant), the following volumes of Brij® 35 stock solution were added: 0.0 mL of Brij® 35 stock solution to prepare R1 diluent containing Brij® 35 at a final concentration of 0.0 g/L; 0.233 mL of stock solution to prepare R1 diluent containing Brij® 35 at a final concentration of 0.14 g/L; 0.466 mL of stock solution to prepare R1 diluent containing Brij® 35 at a final concentration of 0.28 g/L; and 0.699 mL of stock solution to prepare R1 diluent containing Brij® 35 at a final concentration of 0.42 g/L. The solutions were mixed and stored in polypropylene screw-top test tubes.

For test runs, normal blood samples were collected in Vacutainer™ tubes and were anticoagulated with $K_3$EDTA. Samples were assayed in the open tube mode. Unopened samples from the same donor set were stored at room temperature overnight and were assayed on day 2 (i.e., Day 2 samples). Data were collected using an automated hematology analyzer with manual aspiration. Standard runs were at 102 samples/hour; test runs were at 120 samples/hour. For runs which contained 5 pairs of duplicates, the standard deviation, SD, (pooled SD over multiple donors) was calculated for the peroxidase channel parameters using the following equation: $SD=[Sum(d^2)/2N]^{1/2}$, where d is the difference between duplicate values obtained with a particular reagent, and N is the number of samples in the set.

Table 4 depicts a summary of the numerical data obtained from these experiments. The performance of test reagents 1–4 for R1 of the peroxidase method was compared with performance using a standard R1 reagent in the peroxidase method (i.e., the standard R1 reagent contained SDS at a concentration of 0.105 g/L). For Day 1 blood sample analyses, the test reagents generally yielded unacceptable results. For reagent 1, (i.e., a peroxidase R1 reagent comprising neither Brij® nor SDS), no differential data were obtained as a result of severe interference caused by unlysed red cells. For test Px R1 reagents 2 to 4 (i.e., reagent 2: Brij® 35 concentration=0.14 with no SDS; reagent 3: Brij® 35 concentration=0.28 with no SDS; reagent 4: Brij® 35 concentration=0.42 g/L with no SDS), there were a significant number of accuracy and imprecision failures (indicated by asterisks) compared with the method specifications. For reagents 1, 2, and 3, the percent Noise was high (i.e., >34%). The numerical data were also unacceptable for Day 2 blood samples using test reagents comprising only Brij® 35 and no SDS. Thus, the numerical data show that test reagent sets, including peroxidase method R1 reagents which contained Brij® 35 (0.14–0.42 g/L and no SDS), yielded unacceptable performance.

TABLE 4

Analyses of Peroxidase R1 Reagent Compositions Containing Higher Concentrations of Brij ® 35 and no SDS

| REAGENTS | WBCP | % Neut | % Lys | % M | % Eos | % LUC | % Nois |
|---|---|---|---|---|---|---|---|
| DAY 1 SAMPLES | | | | | | | |
| Standard | 5.27 | 56.9 | 28.5 | 8 | 3.7 | 2.1 | 23.71 |
|  | 0.117 | 0.75 | 0.34 | 0.74 | 0.38 | 0.29 | 0.6 |
| 1: No SDS | 15.25 | ND | ND | ND | ND | ND | 89.5 |
| No Brij ® | *0.545 | | | | | | 0.43 |
| 2: No SDS | 5.36 | *61.9 | *21.7 | *9.7 | 3.7 | 2.1 | 47.7 |
| Brij ® : 0.14 g/L | 0.16 | *1.65 | *1.45 | 0.82 | 0.4 | 0.28 | 1.44 |
| 3: No SDS | 5.36 | 57.3 | 28.6 | 7.9 | 3.6 | 1.9 | 34 |
| Brij ® : 0.26 g/L | 0.154 | *1.73 | *1.66 | 0.59 | 0.22 | *0.55 | 2.66 |
| 4: No SDS | 4.77 | *53.2 | *27.3 | *10.1 | 3.5 | *5.1 | 19.2 |
| Brij ® : 0.42 g/L | *1.569 | *7.47 | *6.11 | *1.83 | *0.57 | *2.52 | 4.75 |
| acc spec | 0.15 | 1 | 0.5 | 0.5 | 0.2 | 0.5 | N/A |
| SD spec | 0.16 | 1.4 | 1.1 | 09 | 0.5 | 0.5 | |
| DAY 2 SAMPLES | | | | | | | |
| Standard | 5.19 | 60.6 | 27 | 7.2 | 2.6 | 1.8 | 29.8 |
|  | 0.081 | 1.43 | 0.82 | 0.49 | 0.61 | 0.29 | 3.66 |
| 1: No SDS | ND | ND | ND | ND | ND | ND | 60.1 |
| No Brij ® | | | | | | | 5.77 |
| 2: No SDS | 6.75 | 66.7 | 16.4 | 12.8 | 1.8 | 1.2 | 44.9 |
| Brij ® : 0.14 g/L | 0.509 | 3.41 | 3.97 | 0.86 | 0.19 | 0.18 | 3.82 |
| 3: No SDS | 5.4 | 57.6 | 29 | 9.1 | 1.9 | 1.7 | 33.4 |
| Brij ® : 0.26 g/L | 0.177 | 2.76 | 1.6 | 1.18 | 0.76 | 0.23 | 2 |
| 4: No SDS | 5.27 | 55.4 | 26.7 | 10.7 | 1.6 | 4.6 | 15.2 |
| Brij ® : 0.42 g/L | 0.25 | 2.57 | 1.96 | 1.15 | 0.28 | 2.61 | 2.93 |
| aged acc spec | 0.32 | 2.8 | 2.2 | 1.6 | 1 | 1 | N/A |

In Table 6, the asterisk indicates that the value obtained exceeded the accuracy specification ("acc spec") of the automated analyzer used to perform the method. "ND" indicates that no acceptable or useful data were obtained. "WBCP" indicates the white blood cell count determined from the peroxidase method; "% Neut" indicates percent neutrophils; "% Ly" indicates percent lymphocytes; "% M" indicates percent monocytes; "% Eos" indicates percent eosinophilis; "LUC" indicates percent large unstained cells; and "% Nois" indicates percent origin noise. A representative set of cytograms from the Day 1 and Day 2 blood sample analyses described in Example 2 is displayed in FIGS. 2A–2J. FIGS. 2A–2E represent Day 1 blood sample analyses. FIGS. 2F–J represent Day 2 blood sample analyses. As described, blood samples were withdrawn in Vacutainer™ tubes containing $K_3$EDTA. The reagents used in these analysis correspond to the resulting cytograms as follows: FIG. 2A (Day 1 blood sample) and FIG. 2F (Day 2 blood sample): standard R1 reagent comprising 0.12 g/L Brij® 35 and 0.105 g/L SDS; FIG. 2B (Day 1 blood sample) and FIG. 2G (Day 2 blood sample): SDS-free test reagent 1 comprising 0.0 g/L Brij® 35 and 0.0 g/L SDS; FIG. 2C (Day 1 blood sample) and FIG. 2H (Day 2 blood sample): SDS-free test reagent 2 comprising 0.14 g/L Brij® 35 and 0.0 g/L SDS; FIG. 2D (Day 1 blood sample) and FIG. 2I (day 2 blood sample): SDS-free test reagent 3 comprising 0.28 g/L Brij® 35 and 0.0 g/L SDS; and FIG. 2E (Day 1 blood sample) and FIG. 2J (Day 2 blood sample): SDS-free test reagent 4 comprising 0.42 g/L Brij® 35 and 0.0 g/L SDS.

In the analyses of day 1 blood samples, the cytograms obtained using a Px R1 reagent composition comprising Brij® 35 at 0.12 g/L and SDS at 0.105 g/L were acceptable. However, when neither Brij® nor SDS was present (e.g., reagent 1), the result was a gross failure of the method and no differential count information was obtained; the cytogram showed a very dense noise area and very few white blood cells were detected (FIG. 2B). The failure of the method using reagent 1 can be attributed to the absence of surfactants leading to a large number of unlysed red cells which were cross-linked and contributed to the high level of origin noise. A possible reason for the high noise level may be that surfactants are apparently required to increase the permeability of white cells to the peroxidase substrates; in the absence of surfactant(s), there is likely to be effective inhibition of the staining reaction which occurs inside the white blood cells.

Reagents 2 (FIG. 2C), 3 (FIG. 2D) and 4 (FIG. 2E) yielded approximately the same unacceptable cytogram results as described for reagent 1. In these cases, the cytograms revealed no "valley" (i.e., a clear zone between the dense zones) between lymphocytes and noise, and revealed diffuse cell clusters and a wide "trunk" (i.e., the roughly vertical column which includes both noise and lymphocytes). As the concentration of Brij® increased, the density of the trunk lessened, but the diffuseness of the cell populations increased.

In general, Day 2 or aged samples showed deterioration in the cytograms compared with the corresponding results for fresh blood. In the analyses of such Day 2 samples, cells became leaky so that the cytogram depictions of discrete populations of cell became more diffuse. This was especially accentuated for neutrophils. As for Day 1 samples, reagent 1 yielded gross failure of the method (FIG. 2G). The density of the trunk tended to decrease with increasing concentration of Brij® in the Px R1 reagent solution (FIGS. 2H–2J). Reagents 2, 3, and 4 did not show a valley in the cytogram and there was strong distortion in the differential counts obtained with reagents 2 (FIG. 2H) and 4 (FIG. 2J).

The results of these experiments demonstrated that test peroxidase R1 reagent compositions which contained only nonionic surfactant, i.e., Brij® 35 at concentrations of 0.14–0.42 g/L, and no SDS, yielded unacceptable numerical data and cytograms when used with a Brij®-free rinse solution in the rinse cycle. Similarly, as determined in Example 1, a Px R1 diluent which contained SDS only (0.16–0.20 g/L) and no Brij® 35 was also not an effective reagent when used with the rinse solution that did not contain Brij® (e.g., a Brij®-free rinse). It was thus concluded that Px R1 diluent containing either an ionic surfactant or a nonionic surfactant will not provide acceptable results in the Px method. Indeed, the present discovery showed that both ionic surfactant (e.g., SDS) and nonionic surfactant (e.g., Brij® 35) must be formulated into the Px R1 reagent composition in order achieve accurate and precise results in the method. The present invention also provided the knowledge and finding that such a peroxidase R1 reagent composition was particularly important when used in conjunction with a rinse sample cycle comprising a rinse solution that contained no nonionic surfactant such as Brij® 35, described in further detail in Example 3 hereinbelow.

Example 3

Formulation and testing of a peroxidase R1 diluent reagent composition containing both nonionic surfactant and ionic surfactant A third type of R1 reagent composition was prepared to test the formulation of both nonionic surfactant and ionic surfactant in the peroxidase composition and method. To formulate R1 diluents containing dual surfactants, Brij® 35 at concentrations of 0.080 g/L, 0.12 g/L, and 0.16 g/L was formulated into the R1 diluent composition which also contained SDS at 0.105 g/L. The dual-surfactant-containing reagent composition was used to test both Day 1 and Day 2 blood samples using the peroxidase method of leukocyte differential counting.

An experiment was performed to test this R1 reagent formulation on a sample set of five bloods drawn in Vacutainer™ tubes containing $K_3$EDTA. Both Day 1 and Day 2 samples were assayed with a standard reagent set at 102 samples/hour on an automated analyzer. In addition, both Day 1 and Day 2 samples were assayed with test Px R1 reagents containing both 0.105 g/L of SDS and 0.080, 0.12, and 0.16 g/L of Brij® 35 at 120 samples/hour. For the Day 2 samples, the standard Px R1 reagent contained 0.105 g/L of SDS and no Brij® 35 and was used with a rinse solution containing the surfactant Pluronic® P105 in phosphate buffered saline for comparison with the test R1 reagent formulations.

Accuracy and precision data were obtained (see Table 5 and FIGS. 3A–3D). For Day 1 samples, both precision and accuracy were within method specifications for all peroxidase channel parameters. For Day 2 samples, accuracy (versus Day 1 samples and standard) was acceptable for the test reagents that contained SDS and Brij® 35 at 0.12 g/L and 0.16 g/L. With SDS and 0.080 g/L of Brij® 35, the % neutrophil count was outside the accuracy specification. The above-mentioned standard Px reagent and rinse at 120 samples/hour yielded unacceptable accuracy results with the familiar pattern of elevated WBCP and % lymphocytes, and depressed % neutrophils.

This experiment illustrates that acceptable precision and accuracy were obtained for Day 1 and Day 2 samples with test Px R1 reagent solutions containing SDS at a concentration of 0.105 g/L and Brij® 35 at a concentration range of 0.12 g/L to 0.16 g/L.

FIG. 3A depicts the acceptable results of a leukocyte differential analysis on Day 1 blood samples employing the peroxidase method. The R1 reagent composition for the analysis shown in FIG. 3A is a standard and contained 0.105 g/L of SDS; the standard rinse reagent contained 3.0 g/L of Brij® 35 and 2.0 g/L of SDS. FIG. 3B depicts the performance results of a test Px method using Day 1 blood samples in which the Px R1 reagent composition contained 0.105 g/L of SDS and the rinse reagent contained 2.0 g/L of SDS and no Brij® 35. FIG. 3C depicts the performance results of a test Px method using Day 2 blood samples in which the Px R1 reagent composition contained 0.105 g/L of SDS and the rinse reagent contained 2.0 g/L of SDS and no Brij® 35. FIG. 3D depicts the performance results of a test Px method using Day 2 blood samples in which the Px R1 reagent composition contained both 0.12 g/L of Brij® 35 and 0.105 g/L of SDS, and the rinse reagent contained no SDS and no Brij® 35, but instead contained the rinse reagent composition described herein (Table 2) comprising the nonhemolytic surfactant Pluronic® P105. As can be seen from a comparison of FIG. 3C with FIG. 3D, there is a significant decrease in the thickness of the noise area when the nonionic surfactant Brij® 35 was present in the R1 reagent composition.

appropriate for the condition and volume of the blood sample, resulted in a significant improvement in the performance of peroxidase differential counting method, as well as in the accuracy, precision, and acceptability of the results obtained therefrom.

Example 4

Selection of an optimal concentration range for nonionic surfactant in the R1 reagent composition for use in the Px a method employing a sample rinse cycle and rinse solution free of lyric nonionic surfactant such as Brij® 35

Experiments were performed to select an optimal concentration range for the nonionic surfactant in a peroxidase R1 reagent composition using Brij® 35 as the exemplary

TABLE 5

Effect of the Presence of Both Nonionic Surfactant (Brij ® 35) and Ionic Surfactant (SDS) in the Aqueous Peroxidase R1 Reagent Composition

| Sample‡ | SDS† | Brij ® 35†† | WBCP | % Neut | % Lymph | % Mono | % Eos | % LUC |
|---|---|---|---|---|---|---|---|---|
| Day 1 | 0.105 | 0 | 6.31 | 59.1 | 30.5 | 5.4 | 2.8 | 1.6 |
| (Std) | | | 0.10 | 1.0 | 0.8 | 0.5 | 0.3 | 0.4 |
| Day 1 | 0.105 | 0.080 | 6.23 | 59.6 | 30.0 | 5.4 | 3.1 | 1.5 |
| (Test) | | | 0.04 | 0.3 | 0.4 | 0.4 | 0.2 | 0.1 |
| Day 1 | 0.105 | 0.12 | 6.12 | 59.3 | 29.7 | 6.1 | 2.8 | 1.6 |
| (Test) | | | 0.05 | 0.5 | 0.3 | 0.8 | 0.2 | 0.2 |
| Day 1 | 0.105 | 0.16 | 6.09 | 59.6 | 29.7 | 6.2 | 2.6 | 1.3 |
| (Test) | | | 0.05 | 1.1 | 0.7 | 0.3 | 0.3 | 0.1 |
| Day 2 | 0.105 | 0 | 6.46 | 59.9 | 29.2 | 7.0 | *1.6 | 1.6 |
| (Std) | | | | | | | | |
| Day 2 | 0.105 | 0 | *9.53 | *44.0 | *45.6 | 6.6 | *1.3 | 1.8 |
| (Test) | | | | | | | | |
| Day 2 | 0.105 | 0.080 | 6.332 | *56.0 | 30.7 | 6.8 | *1.7 | 1.2 |
| (Test) | | | | | | | | |
| Day 2 | 0.105 | 0.12 | 6.17 | 60.0 | 29.5 | 7.2 | *1.5 | 1.3 |
| (Test) | | | | | | | | |
| Day 2 | 0.105 | 0.16 | 6.15 | 61.1 | 28.0 | 7.6 | *1.5 | 1.2 |
| (Test) | | | | | | | | |

‡: Day 1 blood samples were used less than 8 hours postdraw; Day 2 blood samples were aged at room temperature for 24 hours. Five samples were assayed in duplicate with each reagent.
*Numerical value exceeded the system specification for aged blood samples.
†,††: Std: Standard, Brij ® 35 and SDS concentrations in the R1 Reagent Solution are in gram/L.
WBCP: White Blood Cell Count in the Peroxidase Method; % Neut: % Neutrophils in sample; % Lymph: % Lymphocytes in sample; % Mono: % Monocytes in sample; % Eos: % Eosinophils in sample; % LUC: % large unstained cells in sample.

As determined from FIGS. 3A and 3B, for Day 1 blood samples using a Px R1 reagent composition containing ionic surfactant (i.e., SDS) only, and a rinse reagent formulation either with or without Brij®, the origin noise was considered to be normal and acceptable. However, a different result was observed when Day 2 samples aged at room temperature were analyzed. For such aged blood sample analysis, a Px R1 reagent comprising 0.105 g/L SDS combined with a rinse reagent comprising no Brij® 35 and 2.0 g/L of SDS produced a cytogram that revealed unacceptable origin noise (FIG. 3C). Interestingly and in accordance with the inventive discovery herein, the noise problem for Day 2 samples was ameliorated by the addition of nonionic surfactant (e.g., Brij® 35) to the peroxidase R1 reagent in the Px method (FIG. 3D). More particularly, the Px R1 reagent composition used in FIG. 3D comprised 0.12 g/L Brij® 35 and 0.105 g/L SDS, and the rinse reagent employed contained neither Brij® nor SDS, but did contain the nonhemolytic surfactant Pluronic® P105. Thus, the discoveries of the appropriate concentrations of nonionic and ionic surfactants to use in the peroxidase R1 reagent composition, and the optimal use of a sample rinse cycle and corresponding rinse reagent comprising a nonhemolytic surfactant such as Pluronic® P105, such that the final nonionic surfactant concentration was nonionic surfactant and using a reagent configuration which included a rinse free of nonionic surfactant such as Brij® 35 (Table 2).

The performance data were generated from experiments in which Brij® 35 was used at the final concentrations of 0.10, 0.12, and 0.14 g/L on two sample sets: 1) 26 non-hospital samples and 2) 14 hospital samples. Data were obtained on both Day 1 and Day 2 samples collected and stored in Vacutainer™ tubes in the presence of $K_3$EDTA as anticoagulant. Both numerical and cytogram data were considered.

The Px R1 test reagent solutions containing 0.10, 0.12, and 0.14 g/L of Brij® 35 were generated by the addition of 0.085, 1.02, and 1.19 mL, respectively, of 30 g/L of Brij® 35 into aliquots of the peroxidase R1 reagent mixture (minus surfactant). A rinse solution containing non-lyric Pluronic® surfactant as described herein was used in the sample rinse cycle employed following the performance of the steps of the peroxidase method using the various R1 test reagent sets. For the standard or control reagent configuration, an R1 diluent containing 0.105 g/L of ionic surfactant SDS in the absence of nonionic surfactant was used, and a rinse reagent solution comprising both Brij® 35 and SDS was used. Non-hospital blood samples were obtained from presumed normal volunteers, and hospital samples were obtained from patients at the Westchester County Medical Center, New York.

Data were collected using an automated hematology analyzer (e.g., the TECHNICON H•™ series) with manual open-tube aspiration. Duplicate Day 1 samples were assayed with each reagent set. Unopened samples from the same donor set were stored at room temperature overnight and were assayed manually with open-tube aspiration on day 2 (i.e., Day 2 samples). Software for the standard runs was at 102 samples/hour (s/h). The test samples were run at 120 s/h. The automated system was washed each day prior to running samples according to the general maintenance instructions set forth in the User's Manual. Peroxidase channel gains were set according to the specifications of the analyzer as set forth in the User's Manual. System imprecision was determined with the standard configuration of software and reagents before and after the test reagents were evaluated. One fresh non-hospital blood sample was aspirated ten times, and the mean and standard deviation (SD) were determined (automatically by the system) for all CBC parameters. The SDs were compared to the system's iraprecision specifications for fresh non-hospital blood. This procedure was followed on each day of the study. Test method imprecision was determined off-line by calculating the SD (pooled SD over multiple donors) for the peroxidase channel parameters using the following equation: $SD=[Sum (d^2)/2N]^{1/2}$, where d is the difference between duplicate values obtained with a particular reagent, and N is the number of samples in the set.

The effect of Brij® 35 concentration on the outcome of the peroxidase method of leukocyte differential counting (26 non-hospital samples)

In this experiment, 26 non-hospital samples were tested in the peroxidase method using the above-described standard peroxidase R1 reagent and also using the test peroxidase method R1 reagents containing Brij® 35 at concentrations of 0.10, 0.12, and 0.14 g/L (see Table 6). For Day 1 blood samples, the clinical parameters were insensitive to Brij® 35 concentration. The percent monocytes was low versus the accuracy specification, and the percent noise decreased as the concentration of Brij® 35 increased. With the exception of % Monocytes, all other parameters satisfied the accuracy and precision specifications.

For Day 2 blood samples, the % Eosinophils was below the accuracy specification for aged blood for the standard method and for all three test methods. All other clinical parameters were within the acceptable limits. The % noise response was similar to that observed for the Day 1 samples tested. For this data set, essentially the same numerical data were obtained for Day 1 and for Day 2 samples over the Brij® 35 concentration range of 0.10, 0.12 and 0.14 g/L. Comparison of 0.14 versus 0.10 g/L of Brij® showed a benefit in the reduction of % noise: 13% and 17% for fresh and aged blood, respectively.

Brij® 35 Concentration Variation (14 hospital samples)

In this experiment, the sample set of 14 hospital blood samples was tested with standard peroxidase method reagents and also with test Px R1 reagents which contained 0.10, 0.12 and 0.14 g/L of Brij® 35 (see Table 7). For the Day 1 and Day 2 blood samples, essentially all of the test reagents satisfied the accuracy specification.

TABLE 6

Effect of Variable Brij ® 35 Concentration in the Px Method (26 Non-Hospital Samples)

| Brij ® 35 (g/L) | WBCP | % N | % L | % M | % E | % LUC | % Nois |
|---|---|---|---|---|---|---|---|
| Day 1 Samples | | | | | | | |
| Std | 6.08 | 58.7 | 29.1 | 7 | 2.7 | 1.9 | 21.2 |
| | 0.1 | 1 | *1.4 | 0.5 | 0.2 | 0.2 | 0.6 |
| 0.1 | 6.12 | 58.7 | 29.4 | *6.2 | 2.8 | 2.2 | 25 |
| | 0.12 | 0.9 | 0.9 | 0.5 | 0.4 | 0.2 | 1.4 |
| 0.12 | 6.1 | 58.9 | 29.5 | *6.2 | 2.8 | 2.1 | 22.9 |
| | 0.11 | 1 | 0.8 | 0.5 | 0.3 | 0.2 | 1.3 |
| 0.14 | 6.1 | 58.6 | 29.6 | *6.4 | 2.8 | 2 | 21.7 |
| | 0.12 | 0.8 | 0.7 | 0.6 | 0.2 | 0.3 | 1.4 |
| Day 2 Samples | | | | | | | |
| Std | *6.48 | 59.2 | 29.8 | 6.9 | *1.6 | 1.7 | 27.1 |
| | 0.18 | 4.2 | 4.2 | 0.6 | 0.3 | 5 | 2.3 |
| 0.1 | 6.29 | 57.7 | 31 | 7.1 | *1.6 | 1.8 | 24.9 |
| | 0.14 | 1.5 | 1.7 | 0.7 | 0.2 | 0.4 | 1.8 |
| 0.12 | 6.24 | 58.6 | 29.9 | 7.2 | *1.6 | 1.8 | 23.9 |
| | 0.13 | 1.2 | 1.2 | 0.7 | 0.2 | 0.3 | 2.3 |
| 0.14 | 6.12 | 59.8 | 29.1 | 7 | *1.6 | 1.7 | 20.8 |
| | 0.12 | 1.2 | 1.3 | 0.8 | 0.4 | 0.2 | 1.8 |
| Specifications: | | | | | | | |
| Day 1 SD | 0.16 | 1.4 | 1.1 | 0.9 | 0.5 | 0.5 | none |
| Day 1 acc | 0.15 | 1 | 0.5 | 0.5 | 0.2 | 0.5 | none |
| Day 2 acc | 0.32 | 2.8 | 2.2 | 1.8 | 1 | 1 | none |

The cytograms generated from the hospital and non-hospital data sets were examined qualitatively for the following characteristics: noise/lymphocyte separation; tightness of neutrophil, lymphocyte, monocyte, eosinophil and LUC populations; staining intensity and positioning of the cell populations on the cytogram; variation in the floating low threshold between the noise zone and the lymphocyte zone, and overall general appearance were compared with the cytograms obtained from analyses of blood samples using standard reagents in the peroxidase method. The sample set assayed in the peroxidase method included both Day 1 and Day 2 non-hospital samples (11 samples) and hospital samples (14 samples).

The conclusions deduced from the resulting cytograms were that 0.12 g/L of Brij® 35 in the peroxidase R1 diluent yielded the best overall cytogram in terms of the separation of cell populations and acceptable origin noise level; 0.10 and 0.14 g/L were less desirable than 0.12 g/L, but both were considered to be acceptable for use in the method. For Day 2 samples, 0.10 g/L of Brij® 35 in the Px R1 test diluent resulted in a slightly higher percent noise than did 0.12 g/L of Brij® 35 (i.e., 21.7% versus 16.7% for Day 1 samples, and 18.9% versus 17.7% for Day 2 samples), but the 0.10 g/L Brij® 35 concentration was determined to be better for the analysis of Day 2 blood (i.e., the cell population areas were tighter). Conversely, 0.14 g/L of Brij® 35 in the R1 test diluent resulted in a slightly lower percent noise than did 0.12 g/L of this surfactant (i.e., 16.2% versus 16.7% for Day 1 samples); however, the 0.14 g/L concentration of this surfactant was marginally worse for Day 2 blood samples (i.e., 0.14 g/L of Brij® 35 caused diffuseness in the cell populations due to attack of the cells by the higher surfactant concentration). The results of the qualitative cytogram inspection were consistent with the numerical analyses.

The data from analogous experiments also demonstrated that five different lots of Brij® 35 tested yielded essentially the same performance data for both Day 1 and Day 2 normal and hospital blood samples. Therefore, lot-to-lot variation of Brij® 35 is not expected to be a problem for producing reagents containing this nonionic surfactant. Based upon the combined numerical and

TABLE 7

Effect of Brij ® 35 Concentration Variation in the Px R1 Reagent Composition (14 Hospital Samples)

| Brij ® 35 (g/L) | WBCP | %N | %L | %M | %E | % LUC | % Nois |
|---|---|---|---|---|---|---|---|
| Day 1 Samples | | | | | | | |
| Std | 15.15 | 71.8 | 16.5 | 5.2 | 0.7 | 5.5 | 8.6 |
|  | 0.16 | *2.9 | *3.0 | *1.8 | 0.1 | *2.3 | 0.4 |
| 0.10 | 15.12 | 71.9 | 16.7 | 4.7 | 0.7 | 5.7 | 10.9 |
|  | *0.18 | 1.3 | 0.7 | *1.3 | 0.2 | 0.5 | 0.6 |
| 0.12 | 15.12 | 71.7 | 17.0 | 4.9 | 0.7 | 5.4 | 9.2 |
|  | 0.13 | 0.8 | 1.0 | 0.5 | 0.1 | 0.5 | 0.5 |
| 0.14 | 15.23 | 71.2 | *17.6 | 5.3 | 0.6 | *4.9 | 9.1 |
|  | *0.19 | 0.8 | 1.1 | 0.5 | 0.1 | 2.5 | 0.7 |
| Day 2 Samples | | | | | | | |
| Std | 14.92 | 71.0 | 17.3 | 6.2 | 0.6 | 4.3 | 12.8 |
|  | 0.67 | 2.3 | 4.2 | 1.5 | 0.1 | 1.7 | 1.0 |
| 0.10 | 15.00 | 70.8 | 17.7 | 5.4 | 0.5 | 4.9 | 11.6 |
|  | 0.29 | 0.6 | 1.3 | 0.4 | 0.1 | 9.3 | 2.3 |
| 0.12 | 15.10 | 70.5 | 17.3 | 5.6 | 0.6 | 5.4 | 10.7 |
|  | 0.37 | 1.3 | 1.3 | 0.5 | 0.1 | 0.1 | 1.0 |
| 0.14 | 15.23 | 70.1 | 17.7 | 5.8 | 0.7 | 5.2 | 9.8 |
|  | 0.37 | 1.5 | 2.1 | 2.1 | 0.1 | 1.3 | 1.0 |
| Specifications: | | | | | | | |
| Day 1 SD | 0.16 | 1.4 | 1.1 | 0.9 | 0.5 | 0.5 | none |
| Day 1 acc | 0.15 | 1 | 0.5 | 0.5 | 0.2 | 0.5 | none |
| Day 2 acc | 0.32 | 2.8 | 2.2 | 1.8 | 1 | 1 | none | cytogram results, an optimal concentration range for Brij® 35 in the peroxidase R1 reagent composition was selected to be about 0.10 g/L to about 0.15 g/L, more preferably, about 0.11 g/L to about 0.13 g/L. It is to be understood that the concentration of nonionic surfactant such as Brij® 35 in the reagent composition can be routinely adjusted by the skilled practitioner, depending upon the hematology analysis system employed in carrying out the differential counting method.

Example 5

Avoidance of the problem of variable rinse carryover by the use of a rinse solution containing nonhemolytic surfactant in conjunction with the use of the dual-surfactant-containing R1 reagent composition in the peroxidase method To avoid the problem of variable rinse carryover in performing the peroxidase white blood cell differential method on automated analyzers, the method of the present invention may be further improved by also including a rinse solution that contains nonionic, non-hemolytic surfactant different from the nonionic surfactant contained in the R1 reagent composition of the invention. The rinse solution has been described hereinabove and comprises non-hemolytic surfactant such as Pluronic® P105, which is inactive and nonfunctional in the peroxidase method, and contributes no more than a slight volume increase to the method. Intersample rinsing alleviates the formation of deposits and eliminates sample/reagent mixture carryover in the peroxidase reaction chambers after multiple sample aspirations when performing the peroxidase leukocyte differential counting method on semi- and fully-automated hematology analyzers.

A particular illustration of the problem of rinse carryover is as follows: prior to the design of the improved present reagent and method, it was found by the present inventors that about 8–10 μL of rinse solution was left in the reaction chamber after completion of the intersample rinse cycle. When the rinse solution was formulated to contain the nonionic surfactant Brij® 35 in accordance with the present invention, this seemingly small volume of rinse (i.e., 8 to 10 μL) was found to be responsible for adding an mount of Brij® 35 to the R1 phase of the method that was significant enough to adversely affect the cell separation results depicted in the cytogram. For example, when the volume of rinse carryover exceeded about 10 μL, the eosinophil population migrated up into the neutrophil population of the cytogram, and both monocytes and lymphocytes moved down in the cytogram. Moreover, when the volume of rinse carryover was about 13.3 μL, the peroxidase method was completely degraded by the presence of Brij® 35. Since the volume of the Px R1 reagent solution added during the first reaction phase of the method was 0.25 mL, the calculated Brij® 35 concentration during the first reaction phase of the peroxidase method was about 0.093 g/L to 0.120 g/L, which corresponds to a volume of rinse carryover of approximately 8.0 to 10.0 μL.

The quantification of the concentration of Brij® 35 that is transferred to the R1 stage of the Px method via rinse carryover was determined during the course of these tests and is presented as follows: the rinse solution contains 3.0 g/L of Brij® 35. The nominal rinse carryover volume is 10 μL, which is equivalent to 30 μg of Brij® 35. The transfer of 30 μg of Brij® 35 to the R1 phase of the peroxidase method (i.e., 250 μL of peroxidase R1 diluent +12 μL of blood, or ~7 μL of plasma, +10 μL of rinse solution yields a total volume of ~267 microliters), in turn, yields a Brij® 35 concentration of 0.112 g/L during the R1 phase of the method. The test peroxidase R1 reagents were all formulated to contain essentially the same concentration of Brij® 35, which allows the delivery of a constant concentration of this nonionic surfactant in the peroxidase method.

Figure 4B:
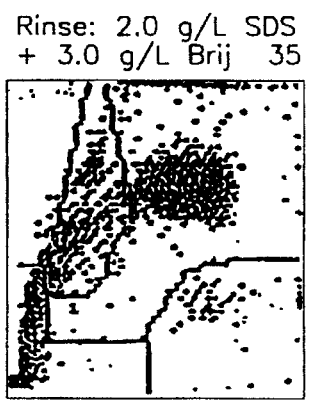
Figure 4C:
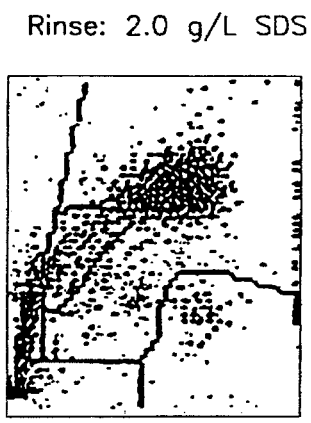
Figure 4D:
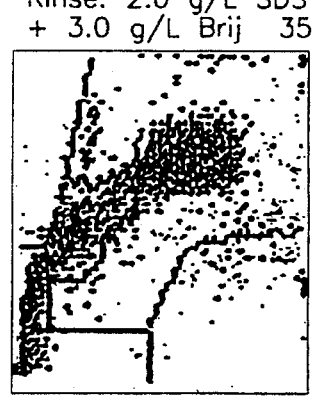
Figure 4E:
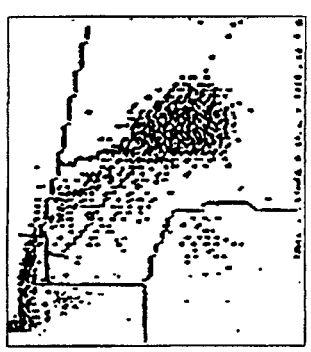
Figure 4F:
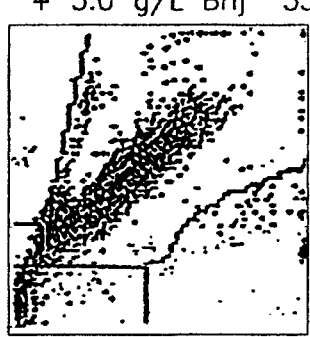

FIGS. 4A–4F demonstrate the effects of variable rinse carryover volume in the peroxidase method of the invention using an aqueous rinse composition without nonionic surfactant, e.g., Brij® 35 (FIGS. 4A, 4C, and 4E) and an aqueous rinse composition with nonionic surfactant (FIGS. 4B, 4D, and 4F). In the R1 and R2 phases of the peroxidase method, as shown in FIGS. 4A–4F, the R1 reagent of the method contained 0.105 g/L of SDS and no Brij® 35. FIGS. 4A and 4B depict cytograms resulting from the performance of the peroxidase method and accompanying rinse cycle, with rinse solution carryover contributing 7.9 μL to the final volume of the peroxidase R1 reagent solution (FIG. 4A: no Brij® 35 in the rinse solution; FIG. 4B: Brij® 35 present in the rinse solution). FIGS. 4C and 4D depict cytograms resulting from the performance of the peroxidase method and accompanying rinse cycle, with rinse solution carryover contributing 10.1 μL to the final volume of the peroxidase R1 reagent solution (FIG. 4C: no Brij® 35 in the rinse solution; FIG. 4D: Brij® 35 present in the rinse solution). FIGS. 4E and 4F depict cytograms resulting from the performance of the peroxidase method and accompanying rinse cycle, with rinse solution carryover contributing 13.3 μL to the final volume of the peroxidase R1 reagent solution (FIG. 4E: no Brij® 35 in the rinse solution; FIG. 4F: Brij® 35 present in the rinse solution). As can be determined from the results, Brij® 35 present in the rinse solution and the contribution of rinse carryover yield a general deterioration of the cytogram results. This result was also observed as rinse carryover volumes increased in the presence of Brij® 35 (FIGS. 4B, 4D, and 4F).

Using the improved reagent composition and method of the invention, carryover was insignificant; in addition, the accuracy and precision of the results were highly acceptable. The nonionic surfactant Brij® 35 was determined by the present inventors to be the agent, which, if present in the rinse composition or solution and if carried over in variable amounts into the peroxidase method, caused unacceptable cytogram results, particularly pronounced in the degradation of the white cell cluster in the cytogram.

As demonstrated herein, the use of nonhemolytic surfactants such as the Pluronics® (e.g., Pluronic® P105) in the rinse solution in the peroxidase method, and the formulation of a new and improved R1 diluent reagent composition of the invention alleviated the effect of variable rinse carryover, maintained an acceptable level of origin noise, and allowed acceptable results to be obtained in the Px method using Day 2 blood samples. Thus, in accordance with the invention, an R1 reagent composition which contains both an ionic surfactant (e.g., SDS) and a nonionic surfactant (e.g., the polyethoxylate Brij® 35) was found by experiment to be useful with blood samples that had been aged for 24 hours or longer at room temperature. Further, in accordance with the invention, the use of a rinse solution containing surfactants like Pluronics® also improved the results obtained from the differential leukocyte differential counting method as described herein.

Example 6

Automated analysis of the leukocyte differential counting method using the R1 reagent composition and peroxidase method This example describes the determination of a rapid (i.e., 120 samples/hour versus 60 or 102 samples/hour) white blood cell differential analysis using an automated hematology analyzer and the improved method and reagent of the invention. It will be clear to those having skill in the art that various analyzers and systems may be used and afforded the benefits described herein using the methods and reagents in accordance with the invention.

Using a whole blood sample, in the R1 reaction phase of the method, 12 µL of sample was delivered with 250 µL of dual-surfactant-containing R1 reagent diluent. About nineteen seconds later, 250 µL of a hydrogen peroxide (3.0 g/L)-containing diluent and 125 µL of a 4-chloro-alpha-naphthol (70 g/L)-containing diluent were added. This is considered the second reaction phase (R2). About thirteen seconds after the addition of the chromogen-containing reagent, the effluent was passed through an electro-optical detection system and a cytogram was prepared. Size and degree of white blood cell staining were measured (forward angle scatter versus absorbance) on a cell by cell basis and plotted on a cytogram. The cytogram was analyzed by computer to obtain the total white blood cell count and the subpopulation differential of neutrophils, eosinophils, monocytes, lymphocytes, and large unstained cells. The figures illustrate cytograms obtained from the electro-optical detection system of an automated hematology analyzer used to carry out the method of the invention on an automated apparatus. The cytograms reveal the types of leukocytes (i.e., WBCs) that are differentiated by the reagent and method of the invention: 1) lymphocytes; 2) monocytes; 3) neutrophils; 4) eosinophils; 5) origin noise resulting from red cell ghosts and platelets, and 6) LUCs (see FIG. 1A).

The final dilution of whole blood was 1:53, and the total reaction time was about 30–32 seconds. A general and nonlimiting example of the thermal profile of the peroxidase method performed on an automated analyzer follows: In the R1 phase of the method, the blood sample and the R1 reagent diluent enter the peroxidase chamber which is preset at about 69° C. ±2° C. During the R1 reaction phase, which has a duration of about 15 to 20 seconds, the temperature increases to about 65° C. to about 75° C., or to about 65° C. to about 70° C. Thereafter, the substrate reagents are added in the second reaction phase of the method (i.e., R2); the R2 temperature is about 50° C. to about 65° C. and has a duration of about 5 to 8 seconds during which time the temperature is increased to about 73° C. ±2° C., which is the final temperature at the completion of the peroxidase method. The rinse solution was used in the rinse cycle after completion of the R2 phase of the peroxidase method. Sample rinse cycles are needed to prevent sample carryover from one sample cycle to another and to prevent buildup in the hydraulics of the automated hematology analyzer systems.

Example 7

Analysis of various nonionic surfactants for suitability in the R1 reagent composition and method of the invention To determine the types of nonionic polyethoxylate surfactants suitable for use in the improved reagent composition and peroxidase method of the invention, the following experiments were performed.

Peroxidase R1 test reagent compositions for use in the first reaction phase of the method were prepared as follows: 200 µL of 3.0 g/L solutions of the various polyethoxylates in distilled water were added to 50.0 mL of the phase 1 reagent composition as described, and placed in 60 mL polypropylene screw-top centrifuge tubes. The surfactant solutions were prepared by adding 3.0 g of polyethoxylate to 97.0 mL of distilled water and stirring with heat until the solution began to boil. After cooling to room temperature for about 30 minutes, 200 µL of the solution were added to the other components of the peroxidase R1 reagent composition to make the R1 test reagents. The polyethoxylates as tested herein are commercially available from various sources; for example, the Brij® surfactants were obtained from ICI and Ruger; the Macol surfactants were obtained from Mazer, the Sipionic surfactants were obtained from Alcolac; the Triton X® surfactants were obtained from Sigma, Union Carbide, or Rohm&Haas; IgepalCO897 was obtained from GAF; Pluronic® P105 was obtained from BASF; Surfonic N31.5 was obtained from Huntsman. For the ionic surfactants, TDAPS was obtained from Boehfinger-Mannheim and TTAB was obtained from Sigma.

As shown in Table 8, the following families or classes of polyethoxylates were used:

TABLE 8

| Surfactant | HLB Value | Hydrophobe | Hydrophile |
|---|---|---|---|
| 1) Straight-chain hydrophobe etherified to polyethylene glycol | | | |
| Brij ® 52 | 5.3 | $C_{16}H_{33}O$ | $POE_2$ |
| Brij ® 30 | 9.7 | $C_{12}H_{25}O$ | $POE_4$ |
| Brij ® 76 | 12.4 | $C_{18}H_{37}O$ | $POE_{10}$ |
| Macol ® TD12 | 14.5 | $C_{13}H_{27}O$ | $POE_{12}$ |
| Siponic ® L12 | 14.6 | $C_{12}H_{25}O$ | $POE_{12}$ |
| Brij ® 78 | 15.3 | $C_{18}H_{37}O$ | $POE_{20}$ |
| Brij ® 58 | 15.7 | $C_{16}H_{37}O$ | $POE_{20}$ |
| Siponic ® E15 | 16.9 | $C_{16}H_{33}O/C_{18}H_{37}O$ | $POE_{32}$ |
| Brij ® 35 | 16.9 | $C_{12}H_{25}O$ | $POE_{23}$ |
| 2) Branched-chain octylphenyl hydrophobe etherified to polyethylene glycol | | | |
| TritonX ® - | 13.5 | $C_8H_{17}OC_6H_4O$ | $POE_{9.5}$ |

TABLE 8-continued

| Surfactant | HLB Value | Hydrophobe | Hydrophile |
|---|---|---|---|
| 100 | | | |
| Triton X® -165* | 15.8 | $C_8H_{17}OC_4O$ | $POE_{16}$ |
| Triton X® -305* | 17.3 | $C_8H_{17}OC_4O$ | $POE_{30}$ |
| Triton X® -405* | 17.9 | $C_8H_{17}OC_4O$ | $POE_{40}$ |
| 3) Straight-chain nonylphenyl hydrophobe etherified to polyethylene glycol | | | |
| Igepal® CO897* | 17.8 | $C_9H_{19}OC_6H_4O$ | $POE_{40}$ |
| 4) Straight-chain fatty acid esterified to polyethylene glycol | | | |
| Myrj® 53 | 17.9 | $C_{17}H_{35}CO_2$ | $POE_{50}$ |

*The raw material was a 70% (w/w) solution in water; therefore, 4.30 g of surfactant solution was mixed with 95.7-g of distilled water to yield a final concentration of 3.00 percent (w/w) of surfactant in the reagent composition of the first reaction phase of the peroxidase method.

Ten blood samples per reagent set were collected from normal donors in Vacutainer® tubes and anticoagulated with $K_3$EDTA. Data were collected on an automated analyzer with manual open-tube aspiration. Duplicate Day 1 blood samples were aspirated with each reagent set. Unopened samples from the same donor set were stored at room temperature overnight and assayed manually on day 2 (Day 2 samples). Software for the standard runs occurred at 102 samples/hour; test samples and reagents were run at a throughput of 120 samples/hour. The system was washed each day prior to running samples according to the operating instructions, and peroxidase channel gains were set according to the operating instructions for the respective automated system being used.

System imprecision was determined with the standard configuration of software and reagents both before and after the test reagents were evaluated. One Day 1 blood sample was aspirated ten times, and the mean and standard deviations were determined (automatically by the system) for all parameters. The standard deviations were compared to the system's imprecision specifications determined for fresh blood. This procedure was followed each day of the study.

To determine test method imprecision, 10 samples were aspirated in duplicate. Imprecision was estimated off-line by calculating the standard deviation, SD, (pooled SD over multiple donors) for peroxidase channel parameters with the following equation: $SD=[Sum(d^2)/2N]^{1/2}$, where d is the difference between duplicate values obtained with a particular reagent, and N is the number of samples in a ten sample set.

The test Px R1 reagents were evaluated in two sets. For each set, a standard peroxidase method (e.g., performed on the TECHNICON H•3™ automated analyzer) was included as the reference. The reference values were defined as Day 1 mean values obtained in the absence of the improved method and reagents of the invention. Accuracy ("acc") for Day 1 and Day 2 sample analysis was determined versus the reference; the accuracy criteria for Day 1 and Day 2 aged blood samples are different. In addition, imprecision was determined only for Day 1 blood samples (see Table 9).

It was noted that Brij® 52 had an HLB of 5.3 (see Table 10), is therefore hydrophobic, and is usually utilized for water-in-oil emulsification applications. The automated peroxidase method performed on the H•3™ automated analyzer utilizes oil-in-water emulsification (i.e., the lipid material of red cell and platelet membranes is "dissolved" by surfactant micelles) in the aqueous environment of the peroxidase effluent).

TABLE 9

Leukocyte Differential Analyses Performed on Day 1 and Day 2 Blood Samples Using Different Nonionic Surfactants

| Reagent | WBCP | % NEUT | % LYMP | % MONO | % EOS | % LUC | % NOISE | HLB | Structure Hydrohobe | Hydrophile POE units n = |
|---|---|---|---|---|---|---|---|---|---|---|
| Day 1 Blood Samples | | | | | | | | | | |
| Std | 6.35 | 61.0 | 26.9 | 6.6 | 2.6 | 2.2 | 17.8 | | | |
| sd | 0.09 | 0.6 | 0.8 | 0.6 | 0.2 | 0.4 | 0.6 | | | |
| Brij® 58 | 6.40 | 60.7 | 27.3 | 6.6 | 2.5 | 2.2 | 19.5 | 15.7 | $C_{16}H_{33}$ | 20 |
| sd | 0.10 | 1.0 | 1.0 | 0.3 | 0.4 | 0.2 | 1.3 | | | |
| Ig.® CO897 | 6.46 | 60.7 | 27.3 | 6.5 | 2.7 | 2.1 | 28.0 | 17.8 | $C_9H_{19}Ph$ | 40 |
| sd | 0.10 | 1.3 | 1.1 | 0.4 | 0.3 | 0.5 | 1.2 | | | |
| Triton X® 100 | 6.32 | 61.0 | 27.1 | 6.6 | 2.7 | 2.0 | 18.9 | 13.5 | $C_8H_{17}Ph$ | 9.5 |
| sd | 0.10 | 1.2 | 0.9 | 0.7 | 0.2 | 0.2 | 1.0 | | | |
| Siponic® E15 | 6.44 | 60.5 | 27.2 | 6.9 | 2.7 | 2.0 | 23.1 | 16,.9 | $C_{16}H_{33}$ and $C_{18}H_{37}$ | **32 |
| sd | 0.14 | 1.3 | 1.0 | 0.3 | 0.3 | 0.3 | 1.4 | | | |
| Triton X® 400 | 6.49 | 61.1 | 27.4 | 6.0 | 2.6 | 2.1 | 27.1 | 17.9 | $C_8H_{17}Ph$ | 40 |
| sd | 0.12 | 1.1 | 1.1 | 0.3 | 0.5 | 1.0 | 1.0 | | | |
| Brij® 76 | 6.50 | 60.8 | 27.1 | 6.4 | 2.7 | 2.3 | 24.3 | 12.4 | $C_{18}H_{37}$ | 10 |
| sd | 0.11 | 0.9 | 0.7 | 0.5 | 0.2 | 0.2 | 0.9 | | | |
| Myrj® 53 | 6.48 | 60.1 | 27.3 | 6.1 | 28 | 2.1 | 24.6 | 17.9 | $C_{17}H_{35}CO_2$ | 50 |
| sd | 0.09 | 1.2 | 1.0 | 0.5 | 0.3 | 0.2 | 0.9 | | | |
| acc spec | 0.15 | 1.0 | 0.5 | 0.5 | 0.2 | 0.5 | none | N/A | | |
| sd spec | 0.16 | 1.4 | 1.1 | 0.9 | 0.5 | 0.5 | none | N/A | | |
| Day 2 Blood Samples | | | | | | | | | | |
| Std | 6.62 | 59.6 | 29.7 | 6.3 | 1.8 | 1.7 | 24.1 | | | |
| Brij® 58 | 6.62 | 60.5 | 28.5 | 7.1 | 1.6 | 1.7 | 14.3 | 15.7 | | |
| Ig® CO897 | *9.79 | *54.4 | *33.7 | 7.3 | *1.3 | 2.3 | 33.0 | 17.8 | | |
| Triton X® 100 | 6.43 | 62.7 | 26.7 | 6.9 | 1.7 | 1.5 | 15.4 | 13.5 | | |

TABLE 9-continued

Leukocyte Differential Analyses Performed on Day 1 and Day 2 Blood Samples Using Different Nonionic Surfactants

| Reagent | WBCP | % NEUT | % LYMP | % MONO | % EOS | % LUC | % NOISE | HLB | Structure Hydrohobe | Hydrophile POE units n = |
|---|---|---|---|---|---|---|---|---|---|---|
| Siponic® E15 | 6.65 | 60.8 | 28.7 | 6.6 | 1.7 | 1.6 | 17.7 | 16.9 | | |
| Triton X® 400 | *10.77 | 57.1 | *31.2 | 7.2 | *1.2 | 2.3 | 33.3 | 17.9 | | |
| Brij® 76 | 6.68 | 60.8 | 28.8 | 6.5 | 1.7 | 1.7 | 23.3 | 12.4 | | |
| Myrj® 53 | *8.04 | 58.8 | *30.5 | 6.7 | *1.2 | 2.0 | 31.8 | 17.9 | | |
| acc spec Day 2 | 0.32 | 2.8 | 2.2 | 1.8 | 1.0 | 1.0 | none | N/A | | |

*exceeded method specification on H•™ analyzer; **calculation based on $C_{17}H_{35}$; sd: mean standard deviation

TABLE 10

Leukocyte Differential Analyses Performed on Day 1 and Day 2 Blood Samples Using Different Nonionic Surfactants

| Reagent | WBCP | % NEUT | % LYMP | % MONO | % EOS | % LUC | % NOIS | HLB | Structure hydrophobe | Hydrophile POE units n = |
|---|---|---|---|---|---|---|---|---|---|---|
| Day 1 Blood Samples | | | | | | | | | | |
| Std | 7.02 | 62.4 | 25.2 | 6.5 | 3.1 | 2.0 | 20.3 | | | |
| sd | 0.14 | 0.8 | 0.7 | 0.5 | 0.2 | 0.2 | 0.5 | | | |
| Brij® 52 | *7.20 | 62.4 | 25.5 | 6.0 | 3.1 | 2.4 | 32.4 | 5.3 | $C_{16}H_{33}$ | 2 |
| sd | 0.09 | 1.0 | 0.8 | 0.6 | 0.2 | 0.4 | 2.0 | | | |
| Brij® 35 | 6.97 | 62.1 | 25.9 | 6.0 | 3.2 | 2.1 | 22.5 | 16.9 | $C_{12}H_{25}$ | 23 |
| sd | 0.15 | 0.7 | 0.6 | 0.5 | 0.3 | 0.3 | 0.8 | | | |
| Siponic® L12 | 6.97 | 61.9 | 25.7 | 6.5 | 3.1 | 2.3 | 19.4 | 14.6 | $C_{12}H_{25}$ | 12 |
| sd | 0.15 | 0.7 | 0.6 | 0.4 | 0.3 | 0.3 | 1.4 | | | |
| Triton X® 165 | 7.04 | 62.1 | 25.7 | 6.1 | 3.2 | 2.2 | 23.0 | 15.8 | $C_8H_{17}Ph$ | 16 |
| sd | 0.09 | 0.7 | 0.9 | 0.7 | 0.2 | 0.3 | 0.7 | | | |
| Triton X® 300 | 7.04 | 62.4 | 25.4 | 6.0 | 3.2 | 2.3 | 27.9 | 17.3 | $C_8H_{17}Ph$ | 30 |
| sd | 0.12 | 1.0 | 0.8 | 0.9 | 0.3 | 0.3 | 1.3 | | | |
| Brij® 30 | 7.05 | 61.5 | 26.1 | 6.5 | 3.1 | 2.1 | 21.0 | 9.7 | $C_{12}H_{25}$ | 4 |
| sd | 0.10 | 0.9 | 0.7 | 0.5 | 0.3 | 0.1 | 0.9 | | | |
| Macol® TD12 | 7.01 | 62.3 | 25.4 | 6.4 | 3.0 | 2.0 | 19.0 | 14.5 | $C_{13}H_{27}$ | 12 |
| sd | 0.15 | 0.9 | 0.7 | 0.5 | 0.3 | 0.1 | 0.9 | | | |
| Brij® 78 | 7.10 | 61.4 | 25.6 | 6.9 | 3.0 | 2.2 | 23.4 | 15.3 | $C_{18}H_{37}$ | 20 |
| sd | 0.16 | 1.2 | 1.0 | 0.6 | 0.3 | 0.3 | 1.2 | | | |
| accy spec | 0.15 | 1 | 0.5 | 0.5 | 0.2 | 0.5 | none | N/A | | |
| sd spc | 0.16 | 1.4 | 1.1 | 0.9 | 0.5 | 0.5 | none | N/A | | |
| Day 2 Blood Samples | | | | | | | | | | |
| Std | 7.16 | 6.3 | 25.8 | 7.4 | 2.2 | 1.7 | 22.4 | | | |
| Brij® 52 | *13.10 | *47.8 | *33.2 | 7.6 | *1.0 | 3.0 | 35.6 | 5.3 | | |
| Brij® 35 | 7.10 | 62.5 | 25.8 | 7.3 | 2.2 | 1.8 | 19.6 | 16.9 | | |
| Siponic® L12 | 6.95 | 62.7 | 25.1 | 7.9 | 2.2 | 1.8 | 14.5 | 14.5 | | |
| Triton X® 165 | 7.07 | 62.6 | 25.7 | 7.2 | 2.3 | 1.7 | 21.9 | 15.8 | | |
| Triton X® 300 | *8.90 | 60.8 | 27.0 | 7.8 | 2.3 | 1.8 | 35.8 | 17.3 | | |
| Brij® 30 | 7.04 | 62.6 | 26.0 | 7.2 | 2.1 | 1.8 | 17.0 | 9.7 | | |
| Macol® TD1 | 6.90 | 63.9 | 24.3 | 7.5 | 2.2 | 1.8 | 13.3 | 14.5 | | |
| Brij® 78 | 7.03 | 63.8 | 25.1 | 6.9 | 2.2 | 1.7 | 17.3 | 15.3 | | |
| acc spec aged | 0.32 | 2.8 | 2.2 | 1.8 | 1.0 | 1.0 | none | N/A | | |

*exceeded method specification on H•™ analyzer; sd: mean standard deviation

In general, the peroxidase effluent comprises the following components: 0.25 mL of the Px R1 reagent solution, Px 1; 0.125 mL of the chromogen-containing reagent solution, Px 2; 0.25 mL of the hydrogen-peroxide-containing reagent solution, Px 3; and 12 μL of blood sample. Px 1 and Px 3 (3.0 g/L aqueous hydrogen peroxide) are aqueous solutions, while Px 2 is a solution of 4-chloro-naphthol dissolved in diethylene glycol (a non-aqueous but water-miscible solvent).

Surfactants with HLBs in the range of 3–6 are recommended for water-in-oil emulsification. In contrast, the recommended HLB range for oil-in-water emulsifications are about 8–18 (M. J. Rosen, 1978, *Surfactant and Interfacial Phenomena*, Wiley-Interscience, pp. 243–244).

Triton X®-305 was shown to be highly hydrophilic as it has an HLB of 17.3 and was suitable for oil-in-water emulsification. However, the suboptimal performance of this surfactant may be a consequence of its extreme hydrophilicity under the conditions of the analysis. As a consequence of their numerous peroxidase studies, the present inventors have observed that red cells become more resistant to lysis after storage at room temperature, due to biochemical changes which occur during storage of the sample. The accuracy and reliability of the newly described methods and reagents are especially important in view of the deterioration of blood samples with time and the need to perform assays on such samples and to obtain adequate results in spite of the less-than-optimal aged sample conditions.

Of the peroxidase R1 reagent compositions containing ionic surfactant plus the following nonionic surfactants: Brij® 58, Igepal® CO897, Triton X®-100, Siponic® E15, Triton X®-405, Brij® 76- and Myrj® 53, all performed accurately and acceptably in the analysis of Day 1 blood samples. However, on Day 2 samples, the Px R1 test reagents containing Igepal® CO897, Triton X®-405, and Myrj® 53 appeared to yield unacceptable numerical and cytogram results (see Tables 11 and 12). These polyethoxylates had HLB values of 17.8, 17.9 and 17.9, respectively, and mean % noise values of 33.0, 33.3 and 31.8, respectively. In addition, other common features in the cytograms resulting from the use of these surfactants were elevated WBCP and distorted % Neutrophils and % Lymphocytes. As indicated, Myrj® 53 is a carboxylic ester of stearic acid, which is likely to be less stable in aqueous solution due to hydrolysis. The abbreviations used in Tables 9 and 10 are: WBCP: % total white blood cells; %NEUT: % neutrophils; LYMPH: % lymphocytes; % MONO: % monocytes; % EOS: % eosinophils; % LUC: % large unstained cells; % NOIS: % origin noise following the performance of the peroxidase method; HLB: hydrophilic lipophilic balance value.

Without being bound in any way by theory, the possible function(s) of surfactant in the R1 reagent composition used in the peroxidase method may include one or more of the following: (1) membrane penetration leading to lysis of red cells and platelets, (2) complexation of water-insoluble 4-chloronapthol, and transport of this substrate into the cells where staining occurs and (3) emulsification of red-cellular debris thereby reducing buildup in the peroxidase channel.

In the representative cytograms depicted in the accompanying figures, the width and darkness (related to the number of cells) of the noise/lymphocyte "trunk" at the origin increased with increasing percent noise. In general, cytograms obtained with aged blood samples exhibit neutrophils which have fallen below the boundaries of the neutrophil population in fresh blood. There is also a tendency for populations to spread out in aged blood. The results from this example showed that the cytograms were comparable among the various families of polyethoxylate surfactants tested (see Table 8, Example 7). In particular, however, the surfactants which derived from surfactant families 1 and 2 (e.g., straight chain or branched octylphenyl hydrophobe etherified to polyethylene glycol), described hereinabove, and having an HLB in the range of about 9.6 to about 16.9 performed in an acceptable manner in the analyses of both Day 1 and Day 2 blood samples. These results are consistent with the generally-recommended surfactant HLB range of about 8-18 for oil-in-water emulsifications. In automated peroxidase methods such as that performed on the exemplary H•3™ system, red cell membrane debris is lipid ("oil") material which is emulsified by surfactant micelles in an aqueous environment; hence, the operative mode for these types of analyses is oil-in-water emulsification.

Example 8

Analysis of surfactants having low HLB values and assessment of Pluronics® for suitability in the Px R1 reagent composition and peroxidase method of leukocyte differential counting Experiments were performed to test the potential utility and effectiveness of polyethoxylate surfactants having a lower HLB range (~8) formulated into Px R1 reagent solutions containing 0.105 g/L of SDS. Accordingly, surfactants having HLB values from 5.3 to 17.9 were tested.

The performance of the test R1 reagent compositions, as a part of a reagent set, was determined with a sample set comprised of five Day 1 non-hospital blood samples and five Day 2 non-hospital samples that were assayed after storage at room temperature. Performance was judged versus current automated analyzer specifications for accuracy and precision. The following parameters were monitored: WBCP, % neutrophils (% N or Neut), % lymphocytes (% Ly), % monocytes (% M), % eosinophils (% Eos), % large unstained cells (% LUCs) and peroxidase noise (% Noise).

Test Px R1 reagents containing SDS, at 0.105 g/L, and the following other surfactants, e.g., Brij® 35, Macol® NP4, Surfonic® N31.5 , Pluronic® P105, Macol® TD3, and Triton X® 35, were prepared according to the procedure described in Example 7. The exemplary test surfactants and their corresponding HLB values are presented:

| Surfactant | HLB Value |
| --- | --- |
| Brij ® 35 | 16.9 |
| Macol ® NP4 | 8.9 |
| Surfonic ® N31.5 | 7.7 |
| Pluronic ® P105 | 12–18 |
| Macol ® TD3 | 8.0 |
| Triton X ® 35 | 7.8 |

Additional studies were conducted to test Pluronics® as replacement surfactants for Brij® 35 as the nonionic surfactant in the peroxidase R1 reagent composition formulated in accordance with the invention.

As described in Example 7 and shown in Tables 9 and 10, acceptable automated peroxidase method results using both Day 1 and Day 2 blood samples were obtained with surfactants having HLB values from about 9.3 to about 16.9. Surfactants having HLB values above about 17.3 as well as low HLB values, e.g., HLB=5.3, in the R1 reagent composition resulted in unacceptable data.

Pluronics®, including P105, possess structures which are distinctly different from the other polyethoxylates used in the experiments as described herein. In the structures of Pluronics®, there are three domains: $(POE)_n$-$(POP)_m$-$(POE)_n$, in which POE and POP represent polyoxyethylene and polyoxypropylene, respectively. The POE domains are hydrophilic (i.e., "the hydrophiles") and the POP domain is hydrophobic (i.e., "the hydrophobe"). There also exists a Pluronic® "reverse" or "R" series, in which there are two POP domains flanking one POE domain, (see Pluronic® & Tetronic® Surfactants, BASF Corporation, 1987). Pluronics® have been assigned HLB values. For P105, the HLB value is 12–18. The wide HLB range assigned to P105 is in sharp contrast to that of the two domain polyethoxylates, which are assigned narrower HLB values. Because the Pluronic structure is significantly different from the other two domain polyethoxylates (polyethoxylated alcohols and phenols), Pluronics® represent a separate class of polyethoxylates. Accordingly, this distinction between two and three domain polyethoxylates allows the utilization of the HLB scale as a predictor of utility for the two domain polyethoxylates as potential nonionic surfactants capable of being employed successfully in the peroxidase reagent and method of the invention.

The two domain class of polyethoxylates can be represented as hydrophobe-O-$(POE)_n$-OH. The hydrophobe can be either a long-chain, branched, or straight alcohol, such as Brij® 35. Alternatively, the other commonly used hydrophobe structures are the octaphenyl (e.g., the Triton X® series) or the nonaphenyl classes (e.g., Triton® series, Macol® NP series, Surfonic® NP series, and the like) in which a straight or branched chain hydrocarbon is bonded to a phenolic structure, which, in turn, is bonded to the POE domain.

When peroxidase R1 reagent compositions were formulated to contain both SDS and polyethoxylated alcohols or phenols having HLB values from about 7.7 to 8.9, and these compositions were used for the analysis of Day 2 blood samples, none of the cytograms exhibited a valley between the lymphocyte region and the noise region. Hence, the percent lymphocytes was high in all four cases and the percent neutrophils was low in three cases. The entire set of such reagents was judged to be unacceptable for use in the R1 reagent composition of the peroxidase method. The most likely cause of the observed unacceptable performance is that these polyethoxylate surfactants were too hydrophobic (i.e., the HLB was too low) for the peroxidase method application using an automated hematology analyzer. Therefore, it was concluded that for polyethoxylated alcohols or phenols, in the presence of an ionic surfactant such as SDS or TDAPS, the required HLB value should be between about 9.3 to about 17.3, more preferably about 9.7 and 16.9. Because Pluronics® represent a separate class of nonionic surfactants and but one member of this class, i.e., Pluronic® P105, was determined not to be useful in the peroxidase reagent and method, it will be appreciated by those in the art, nonetheless, that other Pluronics® having different structures or properties might be useful due to their different HLB values which provide sufficient surfactant lytic properties that are conducive for use in the reagents of the invention.

Accordingly, it was determined from these studies that for two domain polyethoxylate nonionic surfactants at 0.12 g/L, in the presence of 0.105 g/L of SDS in the peroxidase R1 reagent composition, those with HLB values between about 5.3 and about 8.9, and greater than about 17.3, were unacceptable for use in the method. In contrast, surfactants (i.e., those surfactants possessing structures which include the three common types of hydrophobes) formulated into the R1 reagent and having HLB values in the range of about 9.7 to 16.9 provided acceptable results in the method. Pluronics® comprise a distinct class of polyethoxylate surfactants based on their three domain structures. As a consequence of its nonhemolytic characteristics, Pluronic® P105 was not acceptable when formulated into the peroxidase R1 reagent composition at 0.12 g/L (in the presence of 0.105 g/L of SDS), despite the fact that this Pluronic® has been assigned a wide HLB range of 12–18, which overlaps the useful HLB range for the two domain polyethoxylates.

Example 9

Analysis of other classes of ionic surfactants for suitability in the Px R1 reagent composition and peroxidase method of leukocyte differential counting To determine whether or not other classes of ionic surfactants (e.g., cationic or zwitterionic surfactants) were suitable for use in the improved reagent composition and method of the invention, additional experiments were performed employing such ionic surfactants. These studies were designed to test if cationic and zwitterionic surfactants, rather than anionic surfactant such as SDS, were suitable for use in combination with 0.12 g/L of nonionic surfactant (e.g., Brij® 35) in the peroxidase R1 reagent composition. The experiments were performed within the context of an automated hematology analyzer and employed a rinse cycle with a Brij® 35-free rinse. An example of one cationic surfactant tested is tetradecyltrimethylammonium bromide or TTAB; and example of a zwitterionic surfactant tested is tetradecylammoniopropanesulfonate or TDAPS.

Test R1 reagents which did not contain SDS (e.g., Px 1/No SDS) were prepared to contain Brij® 35 (4.0 mL of a 30 g/L solution in distilled water; sorbitol, 113.0 g; NaPhosphate, monobasic, 2.08 g (Mallinkrodt); NaPhosphate, dibasic, 11.89 g (Mallinkrodt); NaCl, 0.488 g (Mallinkrodt 7581KMER); Na$_2$EDTA, 0.750 g (Mallinkrodt 4931KMHK); formaldehyde, 37%, 150 ml (Mallinkrodt). The in-process pH of the assay was 7.23. The test reagents were filtered through a 0.2 micron polysulfone membrane 47 mm disc (Gelman Supor). The ionic surfactants were added to Px 1/no SDS as follows: 200 μL of a 30 g/L solution of either TDAPS or TTAB were added to 50.0 mL of Px 1/No SDS in a 60 ml polypropylene screw-top tube. A rinse reagent containing Pluronic® P105 was used in the rinse cycle of all test analyses. Five normal blood samples per set were collected from normal volunteers in Vacutainer™ tubes and anticoagulated with K$_3$EDTA. Data were collected on an automated hematology analyzer of the TECHNICON H•™ series with manual open-tube aspiration and the method was carried out as described in Example 2.

In the standard or control method of leukocyte differential counting as described herein, the Px R1 reagent composition contained SDS as the sole surfactant and Brij® 35 was found to be supplied to the R1 phase as a result of rinse carryover (i.e., by the rinse which contains both Brij® 35 and SDS, see Example 5). In the test methods conducted in accordance with the findings of the present invention, the Px R1 reagent composition contained both the anionic surfactant SDS and the nonionic surfactant Brij® 35, and the rinse solution contained neither SDS nor Brij®.

The effectiveness of the Px method employing a Px 1 reagent composition in which the anionic surfactant SDS was replaced either by the cationic, quarternary ammonium halide surfactant TrAB at a concentration of 0.12 g/L, or by the zwitterionic surfactant TDAPS at a concentration of 0.12 g/L, was assayed. The results obtained with the R1 reagent containing TTAB at 0.12 g/L and Brij® 35 also at 0.12 g/L ("Reagent 1") were surprising—no peroxidase data were obtained because of poor lysis of the red blood cells which led to a "streak" of red cells on the left side of the cytogram. By contrast, the R1 reagent containing TDAPS at a concentration of 0.12 g/L and Brij® 35 at 0.12 g/L provided acceptable data for both Day 1 and Day 2 blood samples assayed in the peroxidase method (see Table 11). These results demonstrated that zwitterionic surfactants such as TDAPS are suitable for use in conjunction with nonionic surfactant in the Px R1 reagent composition employed in the peroxidase method of the invention.

TABLE 11

Performance of the peroxidase method using a dual-surfactant-containing R1 reagent composition formulated to contain Brij® 35 and either a cationic or a zwitterionic surfactant

| Reagent | Px R1 Surfactant | WBCP | % N | % LYM | % M | % EOS | % LUC | % NOIS | Surf type ‡ | Structure Hydrophobe | Structure Hydrophile |
|---|---|---|---|---|---|---|---|---|---|---|---|
| Day 1 | | | | | | | | | | | |
| Std | SDS | 6.09 | 60.2 | 27.1 | 7.6 | 1.9 | 2.4 | 19.6 | A | $C_{12}H_{25}$—O | $SO_3$— |
| sd | | 0.11 | 0.5 | 0.6 | 0.2 | 0.3 | 0.4 | 0.8 | | | |
| 1 | TTAB and Brij® 35 | | N.D. (non-lysis of red cells) | | | | N.D. | N.D. | C, N | $C_{14}H_{29}$ | $N(CH_3)_3$+ |
| 2 | TDAPS† and Brij® 35 | 6.01 | 61.4 | 27.2 | *5.8 | 2.4 | 2.6 | 20.9 | Z, N | $C_{14}H_{19}$ | |
| sd | | 0.04 | 0.8 | 0.7 | 0.5 | 0.2 | 0.2 | 0.7 | | | |
| acc. spec | | 0.15 | 1 | 0.5 | 0.5 | 0.2 | 0.5 | none | | | |
| sd spec | | 0.16 | 1.4 | 1.1 | 0.9 | 0.5 | 0.5 | none | | | |

| Reagent | | WBCP | % NEU | % LYM | MON | % EOS | % LUC | % NOIS |
|---|---|---|---|---|---|---|---|---|
| Day 2 | | | | | | | | |
| Std | | 5.96 | 61.5 | 25.8 | 8.1 | 1.5 | 2.3 | 17.6 |
| 1 | TTAB and Brij® 35 | N.D. | | N.D. | | N.D. | N.D. | N.D. |
| 2 | TDAPS† and Brij® 35 | 5.81 | 62.0 | 26.6 | 6.6 | *2.0 | 2.1 | 17.2 |
| acc. spec. aged | | 0.32 | 2.8 | 2.2 | 1.8 | 1.0 | 1.0 | none |

*exceeded automated hemotology analyzer specifications.
† TDAPS = N-tetradecyl-N,N-dimethyl-3-ammonio-1-propane-sulfonate.
‡ Surf type: surfactant type; A = anionic (e.g., SDS); C = cationic (e.g., TTAB); Z = switterionic (e.g., TDAPS); and N = nonionic (e.g., Brij® 35).
N.D.: No data obtained due to non-lysis of cells.
$CH_3$—$(CH_2)_{13}$—$N(CH_3)_2$—$(CH_2)_3$—$SO_3$—, hydrophile = —$N(CH_3)_2$—$(CH_2)_3$—$SO_3$—
TDAPS is zwitterionic with a "+" charge on N, and a "–" charge on O
TTAB: tetradecyltrimethylammonium bromide; the counterion is Br—

In summary, for the experiments conducted in Examples 7–9, the polyethoxlated alcohols and phenols with HLB values between about 7.7 and 8.9 were unacceptable as substitutes for the nonionic surfactant Brij® 35 in the Px R1 reagent composition. Plutonic® P105, a block copolymer (polyoxyethylene-polyoxypropylene-polyoxyethylene) was also unsatisfactory (it produced a high 5 Noise in the cytogram) in combination with the ionic surfactant SDS in the Px R1 reagent composition. It is noted that cationic surfactants, e.g., TTAB, were found to be unacceptable substitutes for SDS in the Px R1 reagent composition. However, zwitterionic surfactants, e.g., TDAPS, were found to be acceptable and useful substitutes for SDS.

The contents of all patent applications, issued patents, texts, and published articles and references cited herein are hereby incorporated by reference in their entirety.

As various changes can be made in the above compositions and methods without departing from the scope and spirit of the invention, it is intended that all subject matter contained in the above description, shown in the accompanying drawings, or defined in the appended claims will be interpreted as illustrative, and not in a limiting sense.

What is claimed is:

1. An improved method for determining a differential white blood cell count and subpopulation analysis on a fresh or aged whole blood sample containing red blood cells and white blood cells, said method based on measuring the intrinsic peroxidase activity of white blood cell subpopulations in said sample, comprising the steps of:

a) mixing said blood sample with an aqueous reagent composition to form a uniform reaction mixture, said reagent composition comprising: (i) a nonionic polyethoxylate surfactant at a concentration effective to lyse said red blood cells to release hemoglobin, but not to lyse said white blood cell populations in said sample; (ii) an ionic surfactant of the anionic or zwitterionic class at a concentration effective to lyse said red cells, but not to lyse said white blood cell populations in said sample; (iii) formaldehyde or paraformaldehyde at a concentration effective to chemically crosslink said white blood cells, but not to crosslink said lysable red blood cells in said sample; (iv) a sugar or sugar alcohol at a concentration effective to increase the detectability of lymphocytes in said sample; and (v) a buffer or buffer mixture to maintain a neutral or near-neutral pH of said reaction mixture between about 6.8 to about 8.0;

b) heating said reaction mixture of step a) to a temperature of from about 60° C. to about 75° C., whereby said red blood cells in said sample are lysed and said white blood cells are fixed; and c) staining at least a portion of said white blood cells in said reaction mixture to yield a population of stained white blood cells and a population of unstained white blood cells in suspension; wherein the presence of both said nonionic surfactant and said ionic surfactant in said aqueous reagent mixture provides accurate and reliable white blood cell differential counting results following step c) for fresh blood samples and for aged blood samples that have been stored at room temperature for at least about a day postdraw.

2. The method according to claim 1, wherein said nonionic surfactant of step a) i) has a hydrophilic lipophilic balance or HLB value of between about 9.3 and about 17.5.

3. The method according to claim 2, wherein said HLB value of said nonionic surfactant is between about 9.5 to about 17.3.

4. The method according to claim 3, wherein said HLB value of said nonionic surfactant is between about 9.7 to about 16.9.

5. An improved method for determining a differential white blood cell count and subpopulation analysis on a fresh or aged whole blood sample containing red blood cells and white blood cells, said differential counting method based on the measurement of intrinsic peroxidase activity of white blood cell subpopulations in said sample, comprising the steps of:

a) mixing said blood sample with an aqueous reagent composition to form a reaction mixture, said reagent composition comprising: (i) a nonionic polyethoxylate surfactant having a hydrophilic lipophilic balance or HLB value of between about 9.3 and about 17.5 and present at a concentration effective to lyse said red cells to release hemoglobin, but not to lyse said white blood cell populations in said sample; (ii) an ionic surfactant of the anionic or zwitterionic class at a concentration effective to lyse said red cells, but not to lyse said white blood cell populations in said sample; (iii) formaldehyde or paraformaldehyde at a concentration effective to chemically crosslink said white blood cells, but not to crosslink said lysable red blood cells in said sample; (iv) a sugar or sugar alcohol at a concentration effective to increase the detectability of lymphocytes in said sample; and (v) a buffer or buffer mixture to maintain the pH of said reagent mixture at a neutral or near-neutral pH of between about 6.8 to about 8.0;

b) heating said reaction mixture prepared in step a) to a temperature of from about 60° C. to about 75° C., whereby said red blood cells in said sample are lysed and said whim blood cells are fixed; and c) staining at least a portion of said white blood cells in said reaction mixture to yield a population of stained white blood cells and a population of unstained white blood cells in suspension;

wherein the presence of both said nonionic surfactant and said ionic surfactant in said aqueous reagent mixture provides accurate and reliable whim blood cell differential counting results following step c) for fresh blood samples and for aged blood samples that have been stored at room temperature for at least about a day postdraw.

6. The method according to claim 5, wherein said HLB value of said nonionic surfactant in step a) i) is between about 9.5 to about 17.3.

7. The method according to claim 6, wherein said HLB value of said nonionic surfactant is between about 9.7 to about 16.9.

8. The method according to claim 1 or claim 5, wherein said nonionic polyethoxylate surfactant is selected from the group consisting of straight chain aliphatic hydrophobes etherified to polyethylene glycol; branched chain aliphatic or aromatic octylphenyl hydrophobes etherified to polyethylene glycol; straight chain aliphatic or aromatic nonylphenyl hydrophobes etherified to polyethylene glycol; and straight chain aliphatic fatty acids esterified to polyethylene glycol.

9. The method according to claim 8, wherein said nonionic surfactant is a straight chain aliphatic hydrophobe etherified to polyethylene glycol.

10. The method according to claim 9, wherein said nonionic surfactant is Brij® 35.

11. The method according to claim 8, wherein said nonionic surfactant is a branched chain aliphatic or aromatic hydrophobe etherified to polyethylene glycol.

12. The method according to claim 11, wherein said nonionic surfactant is Triton X®-100.

13. The method according to claim 1 or claim 5, wherein said nonionic polyethoxylate surfactant is present in said aqueous reagent composition of step a) in an amount of about 0.09 g/L to about 0.21 g/L.

14. The method according to claim 1 or claim 5, wherein said ionic surfactant is of said anionic class.

15. The method according to claim 14, wherein said anionic surfactant comprises an alkali metal salt of an alkyl sulfate containing from about 10 to 16 carbon atoms.

16. The method according to claim 15, wherein said anionic surfactant comprises an alkali metal dodecyl sulfate.

17. The method according to claim 16, wherein said anionic surfactant is sodium dodecyl sulfate.

18. The method according to claim 1 or claim 5, wherein said ionic surfactant is of said zwitterionic class.

19. The method according to claim 18, wherein said zwitterionic surfactant is a sulfobetaine.

20. The method according to claim 19, wherein said sulfobetaine is tetradecyldimethylammoniopropanesulfonate or TDAPS.

21. The method according to claim 18, wherein said zwitterionic surfactant is a cholic acid derivative.

22. The method according to claim 21, wherein said cholic acid derivative is 3-[(3-cholamidopropyl)dimethylammonio]-2hydroxy-1-propanesulfonate.

23. The method according to claim 14 or claim 18, wherein said anionic or zwitterionic surfactant is present in the reagent solution of step a) in an amount of about 0.050 g/L to about 0.125 g/L.

24. The method according to claim 1 or claim 5, wherein said aqueous reagent composition of step a) further comprises a chelator of polyvalent metal ions.

25. The method according to claim 24, wherein said polyvalent metal ion chelator is EDTA; EGTA; disodium EDTA or EGTA; trisodium EDTA or EGTA; or tetrasodium EDTA or EGTA at a concentration of about 1 mM to about 5 mM.

26. The method according to claim 1 or claim 5, wherein said reagent composition of step a) further comprises an alkali metal chloride salt.

27. The method according to claim 26, wherein said alkali metal chloride salt in said reagent composition of step a) is selected from the group consisting of NaCl, KCl, and LiCl.

28. The method according to claim 27, wherein said salt is NaCl present in said reagent composition in an amount of from about 6.8 mM to about 10.3 mM.

29. The method according to claim 1 or claim 5, wherein formaldehyde is present in said reagent composition in a concentration of from about 52 g/L to about 58 g/L.

30. The method according to claim 1 or claim 5, wherein said buffer or buffer mixture maintains the pH of said aqueous reagent composition at between about 7.0 to about 7.4.

31. The method according to claim 1 or claim 5, wherein said buffer comprises a buffer mixture of $Na_2HPO_4$ and $NaH_2PO_4$.

32. The method according to claim 1 or claim 5, wherein said staining step involves peroxidase staining of peroxidase-active white blood cells.

33. The method according to claim 32, wherein said staining step comprises rapidly mixing said reaction mixture with hydrogen peroxide and a chromogen.

34. The method according to claim 31, wherein said chromogen is 4-chloro-1-napthol.

35. The method according to claim 1 or claim 5, wherein said sugar or sugar alcohol is selected from the group consisting of sucrose, fructose, dextrose, sorbitol, and mannitol.

36. The method according to claim 35, wherein said sugar alcohol is sorbitol.

37. The method according to claim 36, wherein sorbitol is present in said reagent composition of step a) in an amount of from about 110 g/L to about 120 g/L.

38. The method according to claim 1 or claim 5, further comprising the step of passing the suspension of said stained and unstained white blood cells of step c) through an electro-optical detection system and obtaining a differential white blood cell count of said white blood cells in the suspension.

39. The method according to claim 38, wherein said steps are performed in reaction chambers of an automated hematology analyzer.

40. The method according to claim 39, further comprising the step d) of rinsing said chambers of said automated analyzer with an aqueous rinse reagent composition comprising a nonhemolytic nonionic surfactant that is a copolymer of ethylene oxide and propylene oxide, preferably having a molecular weight of about 950 to about 4000 polyoxypropylene and about 10% to 80% polyoxyethylene, after performing steps a) to c) of said differential counting method.

41. The method according to claim 40, wherein said surfactant comprising said rinse composition is a member of the Pluronic class.

42. The method according to claim 41, wherein said Pluronic is Pluronic P105.

43. The method according to claim 40, wherein said rinse composition further comprises one or more of the following components: an alkali metal chloride salt selected from the group consisting of NaCl, KCl, and LiCl; an antimicrobial compound selected from the group consisting of Proclin 150, Proclin 300, Germall 115, Dowacil 200, and Bronopol; an anti-oxidant compound selected from the group consisting of 3,3+-thiodiproprionic acid, 3,3'-dithioacetic acid, Trolox™ or vitamin E, BHT or 2, 6-di-tert-butyl-4-methylphenol, BHA or 2-tert-butyl-4-methoxyphenol, and MEHQ or ρ-methoxyphenol; and a buffer or buffer mixture to maintain the pH of said aqueous rinse composition at about 6.9 to about 7.6.

44. The method according to claim 40, wherein said aqueous rinse composition has an osmolality of between about 285 mOsmol/kg to about 305 mOsmol/kg.

45. The method according to claim 43, wherein said aqueous rinse composition comprises NaCl, Proclin 150, 3,3'-thiodiproprionic acid, and a buffer or buffer mixture to maintain said pH at about 7.0 to about 7.5.

46. The method according to claim 45, wherein, in said aqueous rinse composition, NaCl is present at a concentration of about 7.40 g/L to 8.0 g/L; Proclin 150 is present at a concentration of about 0.25 mL/L to 0.60 mL/L; and 3,3'-thiodiproprionic acid is present at a concentration of about 50 mg/L to 150 mg/L.

47. An improved reagent composition for lysing red blood cells and staining leukocytes for the determination of a leukocyte differential count and subpopulation analysis of a whole blood sample, said differential count based on measuring endogenous peroxidase activity in subpopulations of said leukocytes in said blood sample, which comprises in aqueous admixture:

a) a nonionic polyethoxylate surfactant at a concentration effective to lyse said red cells to release hemoglobin, but not to lyse said white blood cell populations in said sample;

b) an anionic or zwitterionic surfactant at a concentration effective to lyse said red cells to release hemoglobin, but not to lyse said white blood cell populations in said sample;

c) a sugar or sugar alcohol at a concentration effective to increase the detectability of lymphocytes in said sample;

d) formaldehyde or paraformaldehyde at a concentration effective to chemically crosslink said white blood cells, but not to crosslink said lysable red blood cells in said sample; and e) a buffer or buffer mixture to maintain the pH of said reagent composition at between about 6.8 to about 8.0.

48. The composition according to claim 47, wherein said nonionic surfactant has a hydrophilic lipophilic balance or HLB value of between about 9.3 to about 17.3.

49. The composition according to claim 48, wherein said HLB value of said nonionic surfactant is between about 9.7 to about 16.9.

50. The composition according to claim 47, further comprising a chelator of polyvalent metal ions.

51. An improved reagent composition for lysing red blood cells and staining leukocytes for the determination of a differential leukocyte count and subpopulation analysis of a whole blood sample based on the measurement of endogenous peroxidase activity in subpopulations of said leukocytes in said blood sample, which comprises in aqueous admixture:

a) a nonionic polyethoxylate surfactant having a hydrophilic lipophilic balance or HLB value of between about 9.3 and about 17.5 and at a concentration effective to lyse said red cells to release hemoglobin, but not to lyse said white blood cell populations in said sample;

b) an anionic or zwitterionic surfactant at a concentration effective to lyse said red cells to release hemoglobin, but not to lyse said white blood cell populations in said sample;

c) a sugar or sugar alcohol at a concentration effective to increase the detectability of lymphocytes in said sample;

d) formaldehyde or paraformaldehyde at a concentration effective to chemically crosslink said white blood cells, but not to crosslink said lysable red blood cells in said sample; and e) a buffer or buffer mixture to maintain the pH of said reagent composition at between about 6.8 to about 8.0.

52. The composition according to claim 47 or claim 51, wherein said nonionic polyethoxylate surfactant is selected from the group consisting of straight chain aliphatic hydrophobes etherified to polyethylene glycol; branched chain aliphatic or aromatic octylphenyl hydrophobes etherified to polyethylene glycol; straight chain aliphatic or aromatic nonylphenyl hydrophobes etherified to polyethylene glycol; and straight chain aliphatic fatty acids esterified to polyethylene glycol.

53. The composition according to claim 52, wherein said nonionic surfactant is a straight chain aliphatic hydrophobe etherified to polyethylene glycol.

54. The composition according to claim 51, wherein said nonionic surfactant is Brij® 35.

55. The composition according to claim 52, wherein said nonionic surfactant is a branched chain aliphatic or aromatic hydrophobe etherified to polyethylene glycol.

56. The composition according to claim 55, wherein said nonionic surfactant is Triton X®-100.

57. The composition according to claim 47 or claim 51, wherein said nonionic surfactant is present in said composition in an amount of from about 0.09 g/L to about 0.20 g/L.

58. The composition according to claim 47 or claim 51, wherein said surfactant is an anionic surfactant.

59. The composition according to claim 58, wherein said anionic surfactant comprises an alkali metal salt of an alkyl sulfate containing from about 10 to 16 carbon atoms.

60. The composition according to claim 59, wherein said anionic surfactant comprises an alkali metal dodecyl sulfate.

61. The composition according to claim 60, wherein said anionic surfactant is sodium dodecyl sulfate.

62. The composition according to claim 47 or claim 51, wherein said surfactant is a zwitterionic surfactant.

63. The composition according to claim 62, wherein said zwitterionic surfactant is a sulfobetaine.

64. The composition according to claim 63, wherein said sulfobetaine is tetradecyldimethylammoniopropanesulfonate or TDAPS.

65. The composition according to claim 62, wherein said zwitterionic surfactant is a cholic acid derivative.

66. The composition according to claim 65, wherein said cholic acid derivative is 3-[(3-cholamidopropyl) dimethylammonio]-2hydroxy-1-propanesulfonate.

67. The composition according to claim 47 or claim 51, wherein said anionic or zwitterionic surfactant is present in the composition in an amount of about 0.050 g/L to about 0.125 g/L.

68. The composition according to claim 47 or claim 51, further comprising an alkali metal chloride salt.

69. The composition according to claim 68, wherein said alkali metal chloride salt is selected from the group consisting of NaCl, KCl, and LiCl.

70. The composition according to claim 69, wherein said salt is NaCl and is present in said reagent composition at a concentration of from about 6.8 mM to about 10.3 mM.

71. The composition according to claim 47 or claim 51, wherein formaldehyde is present in said composition in a concentration of from about 52 g/L to about 58 g/L.

72. The composition according to claim 48 or claim 51, wherein said buffer comprises a mixture of $Na_2HPO_4$ and $NaH_2PO_4$.

73. The composition according to claim 47 or claim 51, wherein said sugar or sugar alcohol is selected from the group consisting of sucrose, fructose, dextrose, sorbitol, and mannitol.

74. The composition according to claim 73, wherein said sugar alcohol is sorbitol.

75. The composition according to claim 74, wherein sorbitol is present in said composition at a concentration of from about 110 g/L to about 120 g/L.

76. The composition according to claim 47 or claim 51, further comprising a chelator of polyvalent metal ions.

77. The composition according to claim 76, wherein said polyvalent metal ion chelator is EDTA; EGTA; disodium EDTA or EGTA; trisodium EDTA or EGTA; or tetrasodium EDTA or EGTA.

78. The composition according to claim 77, wherein said chelator is disodium EDTA and is present at a concentration of about 1 mM to about 5 mM.

79. The method according to claim 1 or claim 5, wherein said buffer or said buffer mixture maintains the pH of said aqueous reagent composition at between about 6.9 to about 7.6.

80. The reagent composition according to claim 47 or claim 51, wherein said buffer or said buffer mixture maintains the pH of said aqueous reagent composition at between about 6.9 to about 7.6.

* * * * *